US008814567B2

(12) United States Patent
Zhang et al.

(10) Patent No.: US 8,814,567 B2
(45) Date of Patent: Aug. 26, 2014

(54) DENTAL IMPLANT PROSTHETIC DEVICE WITH IMPROVED OSSEOINTEGRATION AND ESTHETIC FEATURES

(75) Inventors: Kai Zhang, St. Paul, MN (US); Michael Wallick, Warsaw, IN (US); Jeffrey A. Bassett, Vista, CA (US); Michael Collins, San Marcos, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 505 days.

(21) Appl. No.: 11/847,476

(22) Filed: Aug. 30, 2007

(65) Prior Publication Data

US 2008/0050699 A1 Feb. 28, 2008

Related U.S. Application Data

(63) Continuation-in-part of application No. PCT/US2006/033893, filed on Aug. 30, 2006, and a continuation-in-part of application No. 11/622,171, filed on Jan. 11, 2007, now abandoned, which is a continuation-in-part of application No. 11/420,024, filed on May 24, 2006, now abandoned.

(60) Provisional application No. 60/712,577, filed on Aug. 30, 2005, provisional application No. 60/684,743, filed on May 26, 2005.

(51) Int. Cl.
*A61C 8/00* (2006.01)

(52) U.S. Cl.
USPC ............................................ 433/173

(58) Field of Classification Search
USPC ................................. 433/172–176
See application file for complete search history.

(56) References Cited

U.S. PATENT DOCUMENTS

| | | | |
|---|---|---|---|
| 1,929,425 | A | 10/1933 | Hermann |
| 2,721,387 | A | 10/1955 | Ashuckian |

(Continued)

FOREIGN PATENT DOCUMENTS

| | | |
|---|---|---|
| AU | 2006284874 B2 | 3/2012 |
| CA | 2506845 | 7/2004 |

(Continued)

OTHER PUBLICATIONS

The Clinical Assessment of a Ceramic-Coated Transmucosal Dental Implant Collar; International Journal of Prosthodonics; 1996—vol. 9, Issue 5; pp. 466-472.

(Continued)

*Primary Examiner* — Sunil K Singh
(74) *Attorney, Agent, or Firm* — Schwegman Lundberg & Woessner, P.A.

(57) ABSTRACT

Dental implants made at least in part of a porous tantalum material for enhancing the osseointegration of the dental implant into surrounding bone. For example, there is provided a dental implant which includes a porous tantalum portion and an outer portion having a color generally replicating the color of natural teeth. The dental implant further comprises a core portion and the porous tantalum portion at least partially surrounds the core portion. An esthetic portion is disposed at least the outer portion and the porous tantalum portion is disposed for at least partially reinforcing the esthetic portion. After implantation of the implant, bone tissue may osseointegrate into the porous tantalum portion to anchor the implant in position within the surrounding bone. Other embodiments of implants are provided, each implant including at least a portion thereof formed of porous tantalum for improved osseointegration.

26 Claims, 4 Drawing Sheets

(56) References Cited

U.S. PATENT DOCUMENTS

| | | | |
|---|---|---|---|
| 2,857,670 A | 10/1958 | Kiernan, Jr. | |
| 3,314,420 A | 4/1967 | Smith et al. | |
| 3,423,830 A | 1/1969 | Halpern et al. | |
| 3,423,831 A | 1/1969 | Semmelman | |
| 3,497,953 A | 3/1970 | Weissman | |
| 3,685,115 A | 8/1972 | Scott | |
| 3,713,860 A | 1/1973 | Auskern | |
| 3,740,851 A | 6/1973 | Weissman | |
| 3,797,113 A | 3/1974 | Brainin | |
| 3,808,606 A | 5/1974 | Tronzo | |
| 3,849,887 A | 11/1974 | Brainin | |
| 3,851,393 A | 12/1974 | Weiss et al. | |
| 3,896,547 A | 7/1975 | Kulwiec | |
| 3,905,109 A | 9/1975 | Cohen et al. | |
| 3,906,550 A * | 9/1975 | Rostoker et al. | 623/23.55 |
| 3,919,773 A | 11/1975 | Freeman | |
| 3,934,347 A | 1/1976 | Lash et al. | |
| 3,992,725 A | 11/1976 | Homsy | |
| 4,011,602 A | 3/1977 | Rybicki et al. | |
| 4,016,651 A | 4/1977 | Kawahara et al. | |
| 4,086,701 A | 5/1978 | Kawahara et al. | |
| 4,097,935 A | 7/1978 | Jarcho | |
| 4,118,532 A | 10/1978 | Homsy | |
| 4,122,605 A | 10/1978 | Hirabayashi et al. | |
| 4,131,597 A | 12/1978 | Bluethgen | |
| 4,156,943 A | 6/1979 | Collier | |
| 4,178,686 A | 12/1979 | Riess et al. | |
| 4,195,366 A | 4/1980 | Jarcho et al. | |
| 4,199,864 A | 4/1980 | Ashman | |
| 4,229,170 A | 10/1980 | Perez | |
| 4,244,689 A | 1/1981 | Ashman | |
| 4,252,525 A | 2/1981 | Child | |
| 4,259,072 A | 3/1981 | Hirabayashi et al. | |
| 4,281,991 A | 8/1981 | Michi et al. | |
| 4,283,176 A | 8/1981 | Vajda | |
| 4,316,924 A | 2/1982 | Minemura et al. | |
| 4,321,042 A | 3/1982 | Scheicher | |
| 4,331,420 A | 5/1982 | Jones | |
| 4,375,967 A | 3/1983 | Schaefer | |
| 4,379,694 A | 4/1983 | Riess | |
| 4,381,918 A | 5/1983 | Ehmford | |
| 4,411,624 A | 10/1983 | Ogino et al. | |
| 4,431,420 A | 2/1984 | Adair | |
| 4,439,152 A | 3/1984 | Small | |
| 4,448,758 A | 5/1984 | Nagai et al. | |
| 4,475,892 A | 10/1984 | Faunce | |
| 4,478,904 A | 10/1984 | Ducheyne et al. | |
| 4,483,678 A | 11/1984 | Nishio et al. | |
| 4,492,577 A | 1/1985 | Farris et al. | |
| 4,531,915 A | 7/1985 | Tatum, Jr. | |
| 4,531,916 A * | 7/1985 | Scantlebury et al. | 433/173 |
| 4,536,158 A | 8/1985 | Bruins et al. | |
| 4,547,327 A * | 10/1985 | Bruins et al. | 264/16 |
| 4,548,959 A | 10/1985 | Nagai et al. | |
| 4,556,534 A | 12/1985 | Burnett | |
| 4,708,652 A | 11/1987 | Fujiu et al. | |
| 4,713,006 A | 12/1987 | Hakamatsuka et al. | |
| 4,722,688 A | 2/1988 | Lonca | |
| 4,731,085 A | 3/1988 | Koch | |
| 4,737,411 A | 4/1988 | Graves, Jr. et al. | |
| 4,743,260 A | 5/1988 | Burton | |
| 4,744,757 A | 5/1988 | Adai et al. | |
| 4,744,759 A | 5/1988 | Bowen | |
| 4,775,646 A | 10/1988 | Hench | |
| 4,820,157 A | 4/1989 | Salvo | |
| 4,842,517 A | 6/1989 | Kawahara et al. | |
| 4,849,285 A | 7/1989 | Dillon | |
| 4,871,384 A | 10/1989 | Kasuga | |
| 4,872,839 A | 10/1989 | Brajnovie | |
| 4,872,840 A | 10/1989 | Bori | |
| 4,877,400 A | 10/1989 | Holsclaw | |
| 4,880,610 A | 11/1989 | Constantz | |
| 4,906,190 A | 3/1990 | Michna | |
| 4,909,738 A | 3/1990 | Ai et al. | |
| 4,957,554 A | 9/1990 | Mathers et al. | |
| 4,957,819 A | 9/1990 | Kawahara et al. | |
| 4,959,913 A | 10/1990 | Provence et al. | |
| 4,960,733 A | 10/1990 | Kasuga et al. | |
| 4,969,817 A | 11/1990 | Hiranuma et al. | |
| 4,969,913 A | 11/1990 | Ojima | |
| 4,976,738 A | 12/1990 | Frey et al. | |
| 4,983,182 A | 1/1991 | Kijima et al. | |
| 5,000,685 A | 3/1991 | Brajnovic | |
| 5,002,488 A | 3/1991 | Homsy | |
| 5,004,421 A | 4/1991 | Lazarof | |
| 5,007,835 A | 4/1991 | Valen | |
| 5,009,709 A | 4/1991 | Ibsen et al. | |
| 5,049,074 A | 9/1991 | Otani et al. | |
| 5,055,497 A | 10/1991 | Okada et al. | |
| 5,061,285 A | 10/1991 | Koch | |
| 5,062,798 A | 11/1991 | Tsuge et al. | |
| 5,064,731 A | 11/1991 | Miyazaki et al. | |
| 5,076,789 A | 12/1991 | Tanaka | |
| 5,087,200 A | 2/1992 | Brajnovic et al. | |
| 5,120,340 A | 6/1992 | Ducheyne et al. | |
| 5,123,844 A | 6/1992 | Wakai et al. | |
| 5,125,839 A | 6/1992 | Ingber et al. | |
| 5,125,971 A | 6/1992 | Nonami et al. | |
| 5,139,424 A | 8/1992 | Yli-Urpo | |
| 5,152,687 A | 10/1992 | Amino | |
| 5,176,747 A | 1/1993 | Panzera et al. | |
| 5,180,303 A | 1/1993 | Homburg et al. | |
| 5,186,626 A | 2/1993 | Tanaka | |
| 5,192,325 A | 3/1993 | Kijima et al. | |
| 5,194,000 A | 3/1993 | Dury | |
| 5,194,001 A | 3/1993 | Salvo | |
| 5,199,873 A | 4/1993 | Schulte et al. | |
| 5,205,745 A | 4/1993 | Kamiya et al. | |
| D336,683 S | 6/1993 | Inoue et al. | |
| 5,232,365 A | 8/1993 | Ikehara | |
| 5,232,878 A | 8/1993 | Kasuga et al. | |
| 5,236,458 A | 8/1993 | Ducheyne et al. | |
| 5,238,405 A | 8/1993 | Marlin | |
| 5,254,005 A | 10/1993 | Zuest | |
| 5,282,861 A | 2/1994 | Kaplan | |
| 5,282,863 A | 2/1994 | Burton | |
| 5,288,232 A | 2/1994 | Panzera et al. | |
| 5,306,673 A | 4/1994 | Hermansson et al. | |
| 5,308,391 A | 5/1994 | Komma et al. | |
| 5,310,343 A | 5/1994 | Hasegawa et al. | |
| 5,312,254 A | 5/1994 | Rosenlicht | |
| 5,314,334 A | 5/1994 | Panzera et al. | |
| 5,342,201 A | 8/1994 | Oden | |
| 5,344,318 A | 9/1994 | Wilson et al. | |
| 5,344,457 A | 9/1994 | Pilliar et al. | |
| 5,346,397 A | 9/1994 | Braiman | |
| 5,346,937 A | 9/1994 | Kuchler et al. | |
| 5,415,546 A | 5/1995 | Cox, Sr. | |
| 5,419,702 A | 5/1995 | Beaty et al. | |
| 5,425,640 A | 6/1995 | Scharf | |
| 5,427,527 A | 6/1995 | Niznick et al. | |
| 5,439,380 A | 8/1995 | Marlin | |
| 5,443,515 A | 8/1995 | Cohen et al. | |
| 5,449,291 A | 9/1995 | Lueschen et al. | |
| 5,456,723 A | 10/1995 | Steinemann | |
| 5,458,488 A | 10/1995 | Chalifoux | |
| 5,468,544 A | 11/1995 | Marcolongo et al. | |
| 5,476,383 A | 12/1995 | Beaty et al. | |
| 5,549,123 A | 8/1996 | Okuyama et al. | |
| 5,554,665 A | 9/1996 | Tateosian et al. | |
| 5,562,733 A | 10/1996 | Weissbach et al. | |
| 5,571,016 A | 11/1996 | Ingber et al. | |
| 5,572,652 A | 11/1996 | Robusto et al. | |
| 5,575,652 A | 11/1996 | Gaffar et al. | |
| 5,584,693 A | 12/1996 | Nishihara | |
| 5,591,030 A | 1/1997 | Thiel et al. | |
| 5,612,049 A | 3/1997 | Li et al. | |
| 5,614,330 A | 3/1997 | Panzera et al. | |
| 5,621,035 A | 4/1997 | Lyles et al. | |
| 5,624,262 A | 4/1997 | Yarovesky et al. | |
| 5,636,989 A | 6/1997 | Somborac et al. | |
| 5,645,934 A | 7/1997 | Marcolongo et al. | |
| 5,674,069 A | 10/1997 | Osorio | |
| 5,676,745 A | 10/1997 | Kelly et al. | |

(56) References Cited

U.S. PATENT DOCUMENTS

| | | | |
|---|---|---|---|
| 5,683,249 A | 11/1997 | Ibesen et al. |
| 5,685,714 A | 11/1997 | Beaty et al. |
| 5,695,337 A | 12/1997 | Tyszblat Sadoun |
| 5,697,785 A | 12/1997 | Delahaye |
| 5,697,976 A | 12/1997 | Chesterfield et al. |
| 5,697,997 A | 12/1997 | Aronsson et al. |
| 5,698,019 A | 12/1997 | Frank et al. |
| 5,702,346 A | 12/1997 | Lazzara et al. |
| 5,713,994 A | 2/1998 | Kramer et al. |
| 5,723,007 A | 3/1998 | Engel et al. |
| 5,727,943 A | 3/1998 | Beaty et al. |
| 5,755,809 A | 5/1998 | Cohen et al. |
| 5,759,036 A | 6/1998 | Hinds |
| 5,762,500 A | 6/1998 | Lazarof |
| 5,772,438 A | 6/1998 | Deom |
| 5,775,912 A | 7/1998 | Panzera et al. |
| 5,785,524 A | 7/1998 | Wolf |
| 5,833,463 A | 11/1998 | Hurson |
| 5,833,464 A | 11/1998 | Foser |
| 5,839,900 A | 11/1998 | Billet et al. |
| 5,843,348 A | 12/1998 | Giordano |
| 5,849,068 A | 12/1998 | Hofmann, geb. Roth et al. |
| 5,873,721 A | 2/1999 | Willoughby |
| 5,910,273 A | 6/1999 | Thiel et al. |
| 5,915,967 A | 6/1999 | Clokie |
| 5,925,180 A | 7/1999 | Frank et al. |
| 5,931,674 A | 8/1999 | Hanosh et al. |
| 5,934,906 A | 8/1999 | Phimmasone |
| 5,939,211 A | 8/1999 | Mormann |
| 5,947,732 A | 9/1999 | Beaty et al. |
| 5,947,737 A | 9/1999 | Billet et al. |
| 5,947,893 A | 9/1999 | Agrawal et al. |
| 5,951,290 A | 9/1999 | Ardizio et al. |
| 5,951,293 A | 9/1999 | Billet et al. |
| 5,951,295 A | 9/1999 | Lyles et al. |
| 5,961,328 A | 10/1999 | Somborac et al. |
| 5,964,592 A | 10/1999 | Hites et al. |
| 5,971,760 A | 10/1999 | Letcher |
| 5,975,905 A | 11/1999 | Kim et al. |
| 5,984,683 A | 11/1999 | Sakata et al. |
| 5,989,026 A | 11/1999 | Rogers et al. |
| 5,989,027 A | 11/1999 | Wagner et al. |
| 6,010,337 A | 1/2000 | Billet et al. |
| 6,012,923 A | 1/2000 | Bassett et al. |
| 6,013,591 A | 1/2000 | Ying et al. |
| 6,027,742 A | 2/2000 | Lee et al. |
| 6,039,568 A | 3/2000 | Hinds |
| 6,045,361 A | 4/2000 | Misch et al. |
| 6,048,203 A | 4/2000 | Rosenberg |
| 6,048,205 A | 4/2000 | Wright |
| 6,054,400 A | 4/2000 | Brink et al. |
| RE36,689 E | 5/2000 | Beaty et al. |
| 6,056,547 A | 5/2000 | Names |
| 6,063,442 A | 5/2000 | Cohen et al. |
| 6,080,692 A | 6/2000 | Reise et al. |
| 6,087,553 A | 7/2000 | Cohen et al. |
| 6,117,456 A | 9/2000 | Lee et al. |
| 6,120,293 A | 9/2000 | Lazzara et al. |
| 6,126,445 A | 10/2000 | Willoughby |
| 6,126,732 A | 10/2000 | Hofmann et al. |
| 6,135,775 A | 10/2000 | Weisman |
| 6,146,423 A | 11/2000 | Cohen et al. |
| 6,152,737 A | 11/2000 | Beaty et al. |
| 6,159,010 A | 12/2000 | Rogers et al. |
| 6,159,417 A | 12/2000 | Giordano |
| 6,168,435 B1 | 1/2001 | Beaty et al. |
| 6,168,436 B1 | 1/2001 | O'Brien |
| 6,168,633 B1 | 1/2001 | Shoher et al. |
| 6,183,256 B1 | 2/2001 | Fisher et al. |
| 6,183,515 B1 | 2/2001 | Barlow et al. |
| 6,186,791 B1 | 2/2001 | Karmaker et al. |
| 6,193,516 B1 | 2/2001 | Story |
| 6,200,137 B1 | 3/2001 | Holand et al. |
| 6,206,192 B1 | 3/2001 | Winstead et al. |
| 6,214,368 B1 | 4/2001 | Lee et al. |
| 6,224,662 B1 | 5/2001 | Nemeth |
| 6,227,857 B1 | 5/2001 | Morgan et al. |
| 6,235,628 B1 | 5/2001 | Wang et al. |
| 6,244,869 B1 | 6/2001 | Billet et al. |
| 6,250,922 B1 | 6/2001 | Bassett et al. |
| 6,267,597 B1 | 7/2001 | Kim |
| 6,270,347 B1 | 8/2001 | Webster et al. |
| 6,271,282 B1 | 8/2001 | Giordano |
| 6,280,863 B1 | 8/2001 | Frank et al. |
| 6,283,753 B1 | 9/2001 | Willoughby |
| 6,287,341 B1 | 9/2001 | Lee et al. |
| 6,299,448 B1 | 10/2001 | Zdrahala et al. |
| 6,306,784 B1 | 10/2001 | Drescher et al. |
| 6,315,561 B1 | 11/2001 | Baruschke et al. |
| 6,322,728 B1 | 11/2001 | Brodkin et al. |
| 6,325,628 B1 | 12/2001 | Morgan |
| 6,331,312 B1 | 12/2001 | Lee et al. |
| 6,342,202 B1 | 1/2002 | Evans et al. |
| 6,342,302 B1 | 1/2002 | Steidl et al. |
| 6,342,458 B1 | 1/2002 | Schweiger et al. |
| 6,343,930 B1 | 2/2002 | Beaty et al. |
| 6,345,836 B1 | 2/2002 | Wu |
| 6,345,984 B2 | 2/2002 | Karmaker et al. |
| 6,354,836 B1 | 3/2002 | Panzera et al. |
| 6,362,250 B1 | 3/2002 | Karmaker et al. |
| 6,362,251 B1 | 3/2002 | Alkemper et al. |
| 6,379,153 B1 | 4/2002 | Schroering |
| 6,386,876 B1 | 5/2002 | Lee |
| 6,394,806 B1 | 5/2002 | Kumar |
| 6,402,517 B1 | 6/2002 | Hozumi et al. |
| 6,419,491 B1 | 7/2002 | Ricci et al. |
| 6,431,868 B2 | 8/2002 | Story |
| 6,439,890 B1 | 8/2002 | Karmaker et al. |
| 6,447,549 B1 | 9/2002 | Taft |
| 6,450,813 B1 | 9/2002 | McDonald et al. |
| 6,451,292 B2 | 9/2002 | Warford, III et al. |
| 6,454,569 B1 | 9/2002 | Hollander et al. |
| 6,485,849 B2 | 11/2002 | Petticrew |
| 6,495,073 B2 | 12/2002 | Bodenmiller et al. |
| 6,497,573 B2 | 12/2002 | Wagner et al. |
| 6,503,625 B1 | 1/2003 | Rieder et al. |
| 6,514,453 B2 | 2/2003 | Vigliotti et al. |
| 6,527,553 B2 | 3/2003 | Yeung |
| 6,540,784 B2 | 4/2003 | Barlow et al. |
| 6,626,911 B1 | 9/2003 | Engman et al. |
| 6,627,327 B2 | 9/2003 | Reidt et al. |
| 6,641,775 B2 | 11/2003 | Yigliotti et al. |
| 6,648,645 B1 | 11/2003 | MacDougald et al. |
| 6,666,684 B1 | 12/2003 | Names |
| 6,669,476 B2 | 12/2003 | Prestipino et al. |
| 6,679,701 B1 | 1/2004 | Blacklock |
| 6,689,202 B2 | 2/2004 | Panzera |
| 6,743,936 B1 | 6/2004 | Wellinghoff et al. |
| 6,752,863 B2 | 6/2004 | Lyles et al. |
| 6,755,651 B2 | 6/2004 | Brodbeck |
| 6,787,584 B2 | 9/2004 | Jia et al. |
| 6,797,006 B2 | 9/2004 | Hodorek |
| 6,808,659 B2 | 10/2004 | Schulman et al. |
| 6,821,462 B2 | 11/2004 | Schulman et al. |
| 6,846,181 B2 | 1/2005 | Karmaker et al. |
| 6,878,456 B2 | 4/2005 | Castro et al. |
| 6,881,488 B2 | 4/2005 | Giordano |
| 6,932,606 B2 | 8/2005 | Aravena et al. |
| 6,945,448 B2 | 9/2005 | Medlin et al. |
| 6,949,251 B2 | 9/2005 | Dalal et al. |
| 6,953,594 B2 | 10/2005 | Lee et al. |
| 6,976,998 B2 | 12/2005 | Rizzo et al. |
| 6,976,999 B2 | 12/2005 | Charlebois et al. |
| 6,984,261 B2 | 1/2006 | Cummings et al. |
| 6,986,660 B2 | 1/2006 | Kumar et al. |
| 7,011,522 B2 | 3/2006 | Panzera et al. |
| 7,291,012 B2 | 11/2007 | Lyren |
| 7,718,100 B2 | 5/2010 | Soler et al. |
| 8,075,312 B2 | 12/2011 | Collins et al. |
| 8,562,346 B2 | 10/2013 | Collins et al. |
| 2001/0000486 A1 | 4/2001 | Story |
| 2001/0051832 A1 | 12/2001 | Bakker et al. |
| 2002/0028424 A1 | 3/2002 | Prestipino et al. |
| 2002/0039718 A1 | 4/2002 | Kwan |

(56) References Cited

U.S. PATENT DOCUMENTS

| | | |
|---|---|---|
| 2002/0076673 A1 | 6/2002 | Wagner et al. |
| 2002/0095213 A1 | 7/2002 | Bakker et al. |
| 2002/0115742 A1 | 8/2002 | Trieu et al. |
| 2002/0155412 A1 | 10/2002 | Panzera et al. |
| 2002/0160334 A1 | 10/2002 | Brodbeck |
| 2003/0031984 A1 | 2/2003 | Rusin et al. |
| 2003/0068598 A1 | 4/2003 | Vallittu et al. |
| 2003/0073394 A1 | 4/2003 | Reidt et al. |
| 2003/0087984 A1 | 5/2003 | Erbe et al. |
| 2003/0096214 A1 | 5/2003 | Luthardt et al. |
| 2003/0134925 A1 | 7/2003 | Guzauskas |
| 2003/0148247 A1 | 8/2003 | Sicurelli et al. |
| 2004/0024081 A1 | 2/2004 | Trieu et al. |
| 2004/0058299 A1 | 3/2004 | Molin et al. |
| 2004/0064192 A1 | 4/2004 | Bubb |
| 2004/0097627 A1 | 5/2004 | Vallittu et al. |
| 2004/0106085 A1 | 6/2004 | Vallittu et al. |
| 2004/0106087 A1 | 6/2004 | Weigl et al. |
| 2004/0131562 A1 | 7/2004 | Gower et al. |
| 2004/0152034 A1 | 8/2004 | Cummings et al. |
| 2004/0170946 A1 | 9/2004 | Lyren |
| 2004/0185420 A1 | 9/2004 | Schulter et al. |
| 2004/0197737 A1 | 10/2004 | Uckelmann et al. |
| 2004/0234925 A1 | 11/2004 | Benhamou |
| 2004/0241614 A1 | 12/2004 | Goldberg et al. |
| 2005/0008990 A1 | 1/2005 | Ganz et al. |
| 2005/0014108 A1 | 1/2005 | Wohrle et al. |
| 2005/0023710 A1 | 2/2005 | Brodkin et al. |
| 2005/0031704 A1 | 2/2005 | Ahn |
| 2005/0084533 A1 | 4/2005 | Howdle et al. |
| 2005/0084819 A1 | 4/2005 | Sims et al. |
| 2005/0084821 A1 | 4/2005 | Sims et al. |
| 2005/0096652 A1 | 5/2005 | Burton |
| 2005/0100724 A1 | 5/2005 | Seargeant |
| 2005/0109060 A1 | 5/2005 | Cummings et al. |
| 2005/0123672 A1 | 6/2005 | Justin et al. |
| 2005/0184134 A1 | 8/2005 | Charlebois et al. |
| 2005/0191248 A1 | 9/2005 | Hunter et al. |
| 2005/0221259 A1 | 10/2005 | Anderson |
| 2005/0261795 A1 | 11/2005 | Ghosh et al. |
| 2005/0266382 A1 | 12/2005 | Soler et al. |
| 2006/0075826 A1 | 4/2006 | Roberts et al. |
| 2006/0105295 A1 | 5/2006 | Mayer et al. |
| 2007/0015110 A1 | 1/2007 | Zhang et al. |
| 2007/0111165 A1 | 5/2007 | Wallick et al. |
| 2007/0118221 A1 | 5/2007 | Robie et al. |
| 2007/0148321 A1 | 6/2007 | Ashida et al. |
| 2007/0148621 A1 | 6/2007 | Yakir |
| 2007/0184265 A1 | 8/2007 | Ranganathan et al. |
| 2008/0050699 A1 | 2/2008 | Zhang et al. |
| 2008/0241793 A1 | 10/2008 | Collins et al. |
| 2008/0280254 A1 | 11/2008 | Ackermann |
| 2009/0011384 A1 | 1/2009 | Collins et al. |
| 2009/0036908 A1 | 2/2009 | Zokol et al. |
| 2009/0093888 A1 | 4/2009 | Dawson et al. |
| 2009/0098510 A1 | 4/2009 | Zhang |
| 2009/0098511 A1 | 4/2009 | Zhang |
| 2013/0344457 A1 | 12/2013 | Collins et al. |

FOREIGN PATENT DOCUMENTS

| | | |
|---|---|---|
| CA | 2507324 A1 | 11/2005 |
| CA | 2653274 A1 | 12/2007 |
| DE | 3110694 A1 | 9/1982 |
| DE | 4209569 C2 | 11/1994 |
| DE | 19508224 A1 | 9/1995 |
| DE | 19529036 | 3/1997 |
| DE | 10105398 | 8/2002 |
| EP | 0051955 A2 | 5/1982 |
| EP | 0076692 A1 | 4/1983 |
| EP | 0112319 A1 | 6/1984 |
| EP | 0206726 A2 | 12/1986 |
| EP | 0266313 | 5/1988 |
| EP | 0271236 | 6/1988 |
| EP | 0288446 A1 | 10/1988 |
| EP | 0296513 A1 | 12/1988 |
| EP | 0345581 | 12/1989 |
| EP | 0366018 | 5/1990 |
| EP | 0417018 | 3/1991 |
| EP | 0450939 A2 | 10/1991 |
| EP | 0466267 A1 | 1/1992 |
| EP | 0467948 | 1/1992 |
| EP | 0498923 | 8/1992 |
| EP | 0333503 | 2/1993 |
| EP | 0560279 | 9/1993 |
| EP | 560279 A1 | 9/1993 |
| EP | 0806211 | 11/1997 |
| EP | 0950421 | 10/1999 |
| EP | 1281372 | 2/2003 |
| EP | 1598028 | 11/2005 |
| EP | 1712205 A2 | 10/2006 |
| FR | 2138735 A1 | 1/1973 |
| FR | 2796265 | 1/2001 |
| GB | 701802 A | 1/1954 |
| GB | 1526780 | 9/1978 |
| GB | 2045083 A | 10/1980 |
| GB | 2199626 A | 7/1988 |
| GB | 2401867 | 11/2004 |
| GB | 2416996 | 2/2006 |
| JP | 61275205 | 12/1986 |
| JP | 63290559 | 11/1988 |
| JP | 1025849 | 1/1989 |
| JP | 1159832 U | 11/1989 |
| JP | 3292948 A | 12/1991 |
| JP | 7255832 A | 10/1995 |
| JP | 9313505 A | 12/1997 |
| JP | 2000501966 A | 2/2000 |
| JP | 2000514329 A | 10/2000 |
| JP | 2001518348 A | 10/2001 |
| JP | 2002126071 | 5/2002 |
| JP | 4975741 B2 | 7/2012 |
| WO | WO-8604807 A1 | 8/1986 |
| WO | WO-8706842 A1 | 11/1987 |
| WO | 8900410 | 1/1989 |
| WO | 90/11979 | 11/1990 |
| WO | 93/20773 | 10/1993 |
| WO | 94/21190 | 9/1994 |
| WO | WO-9513101 A1 | 5/1995 |
| WO | WO-9513102 A1 | 5/1995 |
| WO | 9528973 | 11/1995 |
| WO | 9721393 | 6/1997 |
| WO | WO-9722308 A1 | 6/1997 |
| WO | 97/41809 | 11/1997 |
| WO | 9741809 | 11/1997 |
| WO | WO-9801081 A1 | 1/1998 |
| WO | 9830170 | 7/1998 |
| WO | WO-9917676 A2 | 5/1999 |
| WO | 0021455 | 4/2000 |
| WO | 01/32072 | 5/2001 |
| WO | 01/87193 | 11/2001 |
| WO | 0234155 | 2/2002 |
| WO | 02/36039 | 5/2002 |
| WO | 02/062901 | 8/2002 |
| WO | 02/064100 | 8/2002 |
| WO | WO-02062901 A1 | 8/2002 |
| WO | WO-02064100 A1 | 8/2002 |
| WO | 03/065996 | 5/2003 |
| WO | 03065939 | 8/2003 |
| WO | 03/078508 | 9/2003 |
| WO | 03/094774 | 11/2003 |
| WO | 2004/054464 | 7/2004 |
| WO | WO-2004054464 A2 | 7/2004 |
| WO | 2004103202 | 12/2004 |
| WO | WO-2006082610 A2 | 8/2006 |
| WO | WO-2007027794 A1 | 3/2007 |
| WO | 2007086832 | 8/2007 |
| WO | WO-2009029711 A1 | 3/2009 |
| WO | WO-2009029718 A1 | 3/2009 |
| WO | WO-2009032759 A1 | 3/2009 |

(56) References Cited

FOREIGN PATENT DOCUMENTS

| WO | WO-2009032766 A1 | 3/2009 |
|---|---|---|
| WO | WO-2010002661 A2 | 1/2010 |
| WO | WO-2010002661 A3 | 1/2010 |

OTHER PUBLICATIONS

Two Applications of Transmucosal Milled Ceramic in Implantology; Preliminary Clinical Examples; Implant Quintessence Dentistry International; Aug. 1996—vol. 27, Issue 8, pp. 533-547.

International Search Report from related PCT/US2008/074655; Feb. 18, 2009, 9 pages.

Shape Optimization of Randomly Oriented Short Fibers for Bone Cement Reinforcements, Yan Zhou, Chaodi Li, James J. Mason, Materials Science & Engineering A 393 (2005) 374-381.

Flocculants, Binders, and Bonds, Chapter 11, Molecular Binders pp. 173-177.

Injection Molding, Chapter 24, Equipment and Material Variables in Injection Molding, pp. 479-481.

An Introduction to Silanes and Their Clinical Applications in Dentistry, Jukka P.I Matinlinna et al., vol. 17, No. 2, 2004 pp. 155-164 The International Journal of Prosthodontics.

Innovative Ceramic-Fiber Technology Energizes Advanced Cerametrics, Richard B. Cass et al. Story—The American Ceramic Society, American Ceramic Society Bulletin, Nov. 2003, pp. 9701-9706.

Peek-Classix, Information Sheet Invibio Ltd., Properties of Peek-Classix White Granular.

Computer-Guided Immediate Provisionalization of Anterior Multiple Adjacent Implants: Surgical and Prosthodontic Rationale, Joseph Y. K. Kan, Practical Procedures & Aethetic Dentistry, vol. 18, No. 10, 617-623, 2006.

Presurgical Planning With CT-Derived Fabrication of Surgical Guides, Scott D. Ganz, J Oral Maxillofac Surg 63:59-73, 2005, Suppl 2.

Prosthetically Directed Implant Placement Using Computer Software to Ensure Precise Placement and Predictable Prosthetic Outcomes. Part 1: Diagnostics, Imaging, and Collaborative Accountability, Alan L. Rosenfeld, International Journal of Periodontics & Restorative Dentistry, vol. 26, No. 3, 2006, 215-221.

Two Applications of Transmuscosal Milled Ceramic in Implantology; Preliminary Clinical Examples; Implant Quintessence Dentistry International; Aug. 1996—vol. 27, Issue 8, pp. 533-547.

International Search Report from related application PCT/US2006/020130, dated Feb. 6, 2007, 10 pages.

International Search Report from related application PCT/US2009/048469, dated Oct. 19, 2009, 9 pages.

International Search Report from related application PCT/US2009/048476; dated Dec. 10, 2009; 13 pages.

International Search Report from related application PCT/US2009/048481; dated Dec. 10, 2009; 13 pages.

International Search Report from related application PCT/US2009/062308; dated Jan. 21, 2010; 17 pages.

"U.S. Appl. No. 11/420,024, Non Final Office Action mailed Apr. 27, 2012", 8 pgs.

"U.S. Appl. No. 12/167,018, Final Office Action mailed Jun. 14, 2012", 19 pgs.

"U.S. Appl. No. 12/167,049, Final Office Action mailed Dec. 17, 2012", 11 pgs.

"U.S. Appl. No. 12/167,049, Notice of Allowance mailed Jun. 24, 2013", 6 pgs.

"U.S. Appl. No. 12/167,049, Response filed Apr. 17, 2013 to Non Final Office Action mailed Dec. 17, 2012", 15 pgs.

"U.S. Appl. No. 12/167,049, Response filed Aug. 28, 2012 to Non Final Office Action mailed Mar. 28, 2012", 18 pgs.

"U.S. Appl. No. 14/010,634, Preliminary Amendment filed Aug. 27, 2013", 3 pgs.

"Australian Application Serial Appl. No. 2006249942, Office Action mailed Aug. 30, 2010", 2 pgs.

"Australian Application Serial No. 2006249942, Response filed May 16, 2011 to Office Action mailed Aug. 30, 2010", 8 pgs.

"Australian Application Serial No. 2006284874, Office Action mailed Jul. 26, 2011", 4 pgs.

"Australian Application Serial No. 2006284874, Preliminary Amendment mailed May 6, 2008", 12 pgs.

"Australian Application Serial No. 2006284874, Preliminary Amendment mailed Oct. 20, 2010", 15 pgs.

"Australian Application Serial No. 2006284874, Response filed Oct. 27, 2011 to Office Action mailed Jul. 26, 2011", 10 pgs.

"Australian Application Serial No. 2007267640, Preliminary Amendment filed Jan. 9, 2009", 16 pgs.

"Canadian Application Serial No. 2,620,427, Office Action mailed Jul. 7, 2013", 3 pgs.

"Canadian Application Serial No. 2,620,427, Response filed Jul. 4, 2013 to Office Action mailed Jan. 7, 2013", 8 pgs.

"European Application Serial No. 06784466.2, Office Action mailed Jan. 12, 2013", 6 pgs.

"European Application Serial No. 06813974.0, Preliminary Amendment filed Mar. 19, 2008", 2 pgs.

"European Application Serial No. 07762308.0, Preliminary Amendment filed Dec. 17, 2008", 3 pgs.

"European Application Serial No. 08798879.6, Office Action mailed May 7, 2010", 2 pgs.

"European Application Serial No. 08798879.6, Preliminary Amendment filed Mar. 30, 2010", 4 pgs.

"European Application Serial No. 08828199.3, Preliminary Amendment filed Mar. 29, 2010", 2 pgs.

"European Application Serial No. 08828675.2, Preliminary Amendment filed Mar. 29, 2010", 2 pgs.

"European Application Serial No. 08829319.6, Preliminary Amendment filed Mar. 29, 2010", 3 pgs.

"European Application Serial No. 09774112.8, Office Action mailed Mar. 27, 2013", 6 pgs.

"European Application Serial No. 09774112.8, Response filed Aug. 6, 2013 to Office Action mailed Mar. 27, 2013", 16 pgs.

"International Application Serial No. PCT/US2006/020130, Written Opinion mailed Feb. 6, 2007", 8 pgs.

"International Application Serial No. PCT/US2007/069562, Written Opinion mailed Nov. 24, 2008", 10 pgs.

"Japanese Application Serial No. 2008-513684, Office Action mailed Jul. 12, 2011", 5 pgs.

"Japanese Application Serial No. 2008-529238, Response filed Mar. 29, 2013 to Office Action mailed Oct. 23, 2012", (W/ English Translation), 7 pgs.

"Japanese Application Serial No. 2008-529238, Office Action mailed Aug. 20, 2013", (W/ English Translation), 7 pgs.

"U.S. Appl. No. 11/420,024, Examiner Interview Summary mailed Jan. 24, 2012", 3 pgs.

"U.S. Appl. No. 11/420,024, Final Office Action mailed Oct. 12, 2012", 5 pgs.

"U.S. Appl. No. 11/420,024, Final Office Action mailed Jan. 21, 2011", 6 pgs.

"U.S. Appl. No. 11/420,024, Non Final Office Action mailed Mar. 29, 2010", 5 pgs.

"U.S. Appl. No. 11/420,024, Non Final Office Action mailed Apr. 27, 2012", 6 pgs.

"U.S. Appl. No. 11/420,024, Non Final Office Action mailed May 10, 2011", 5 pgs.

"U.S. Appl. No. 11/420,024, Non Final Office Action mailed Sep. 11, 2009", 5 pgs.

"U.S. Appl. No. 11/420,024, Response filed Feb. 16, 2011 to Final Office Action mailed Oct. 12, 2010", 9 pgs.

"U.S. Appl. No. 11/420,024, Response filed Feb. 24, 2012 to Final Office Action mailed Nov. 21, 2011", 8 pgs.

"U.S. Appl. No. 11/420,024, Response filed Jun. 4, 2009 to Restriction Requirement mailed May 4, 2009", 2 pgs.

"U.S. Appl. No. 11/420,024, Response filed Jul. 29, 2010 to Non Final Office Action mailed Mar. 29, 2010", 9 pgs.

"U.S. Appl. No. 11/420,024, Response filed Sep. 2, 2011 to Non Final Office Action mailed May 10, 2011", 8 pgs.

"U.S. Appl. No. 11/420,024, Response filed Dec. 8, 2009 to Non Final Office Action mailed Sep. 11, 2009", 8 pgs.

(56) References Cited

OTHER PUBLICATIONS

"U.S. Appl. No. 11/420,024, Restriction Requirement mailed May 4, 2009", 5 pgs.
"U.S. Appl. No. 11/622,171, Advisory Action mailed Sep. 1, 2009", 3 pgs.
"U.S. Appl. No. 11/622,171, Final Office Action mailed Apr. 27, 2009", 10 pgs.
"U.S. Appl. No. 11/622,171, Non Final Office Action mailed Oct. 14, 2008", 10 pgs.
"U.S. Appl. No. 11/622,171, Response filed Jan. 14, 2009 to Non Final Office Action mailed Oct. 14, 2008", 15 pgs.
"U.S. Appl. No. 11/622,171, Response filed Jul. 3, 2008 to Restriction Requirement mailed Jun. 13, 2008", 10 pgs.
"U.S. Appl. No. 11/622,171, Response filed Aug. 7, 2009 to Final Office Action mailed Apr. 27, 2009", 13 pgs.
"U.S. Appl. No. 11/622,171, Restriction Requirement mailed Jun. 13, 2008", 8 pgs.
"U.S. Appl. No. 12/065,259, Final Office Action mailed Dec. 9, 2010", 8 pgs.
"U.S. Appl. No. 12/065,259, Information Disclosure Statement mailed Feb. 28, 2008", 4 pgs.
"U.S. Appl. No. 12/065,259, Information Disclosure Statement mailed May 10, 2010", 3 pgs.
"U.S. Appl. No. 12/065,259, Information Disclosure Statement mailed Aug. 23, 2010", 30 pgs.
"U.S. Appl. No. 12/065,259, Information Disclosure Statement mailed Oct. 18, 2011", 2 pgs.
"U.S. Appl. No. 12/065,259, Non Final Office Action mailed Apr. 27, 2011", 8 pgs.
"U.S. Appl. No. 12/065,259, Non Final Office Action mailed Dec. 21, 2009", 8 pgs.
"U.S. Appl. No. 12/065,259, Notice of Allowance mailed Sep. 16, 2011", 7 pgs.
"U.S. Appl. No. 12/065,259, Response filed Apr. 7, 2011 to Final Office Action mailed Dec. 9, 2010", 10 pgs.
"U.S. Appl. No. 12/065,259, Response filed Jun. 18, 2010 to Non Final Office Action mailed Dec. 21, 2009", 9 pgs.
"U.S. Appl. No. 12/065,259, Response filed Jun. 30, 2011 to Non Final Office Action mailed Apr. 27, 2011", 8 pgs.
"U.S. Appl. No. 12/065,259, Response filed Sep. 30, 2010 to Restriction Requirement mailed Aug. 31, 2010", 7 pgs.
"U.S. Appl. No. 12/065,259, Restriction Requirement mailed Aug. 31, 2010", 5 pgs.
"U.S. Appl. No. 12/167,004, Examiner Interview Summary mailed Mar. 2, 2012", 3 pgs.
"U.S. Appl. No. 12/167,004, Final Office Action mailed Nov. 9, 2011", 16 pgs.
"U.S. Appl. No. 12/167,004, Non Final Office Action mailed Feb. 13, 2012", 17 pgs.
"U.S. Appl. No. 12/167,004, Non Final Office Action mailed May 24, 2011", 17 pgs.
"U.S. Appl. No. 12/167,004, Non Final Office Action mailed Nov. 10, 2010", 12 pgs.
"U.S. Appl. No. 12/167,004, Response filed Feb. 9, 2012 to Final Office Action mailed Nov. 9, 2011", 15 pgs.
"U.S. Appl. No. 12/167,004, Response filed Mar. 10, 2011 to Non Final Office Action mailed Nov. 10, 2010", 14 pgs.
"U.S. Appl. No. 12/167,004, Response filed Aug. 24, 2011 to Non Final Office Action mailed May 24, 2011", 13 pgs.
"U.S. Appl. No. 12/167,004, Response filed Oct. 11, 2010 to Restriction Requirement mailed Sep. 14, 2010", 6 pgs.
"U.S. Appl. No. 12/167,004, Restriction Requirement mailed Sep. 14, 2010", 4 pgs.
"U.S. Appl. No. 12/167,018, Examiner Interview Summary mailed Oct. 23, 2012", 3 pgs.
"U.S. Appl. No. 12/167,018, Final Office Action mailed May 23, 2011", 22 pgs.
"U.S. Appl. No. 12/167,018, Non Final Office Action mailed Aug. 30, 2011", 20 pgs.
"U.S. Appl. No. 12/167,018, Non Final Office Action mailed Nov. 18, 2010", 22 pgs.
"U.S. Appl. No. 12/167,018, Response filed Mar. 18, 2011 to Non Final Office Action mailed Nov. 18, 2010", 11 pgs.
"U.S. Appl. No. 12/167,018, Response filed Aug. 23, 2011 to Final Office Action mailed May 23, 2011", 11 pgs.
"U.S. Appl. No. 12/167,018, Response filed Oct. 27, 2010 to Restriction Requirement mailed Aug. 30, 2011", 6 pgs.
"U.S. Appl. No. 12/167,018, Response filed Nov. 9, 2012 to Final Office Action mailed Jun. 14, 2012", 17 pgs.
"U.S. Appl. No. 12/167,018, Response filed Nov. 22, 2011 to Non Final Office Action mailed Aug. 30, 2011", 10 pgs.
"U.S. Appl. No. 12/167,018, Restriction Requirement mailed Aug. 30, 2010", 6 pgs.
"U.S. Appl. No. 12/167,032 , Response filed Nov. 9, 2012 to Final Office Action mailed Jun. 19, 2012", 11 pgs.
"U.S. Appl. No. 12/167,032, Examiner Interview Summary mailed Oct. 23, 2012", 3 pgs.
"U.S. Appl. No. 12/167,032, Final Office Action mailed Apr. 27, 2012", 17 pgs.
"U.S. Appl. No. 12/167,032, Final Office Action mailed Jun. 19, 2012", 14 pgs.
"U.S. Appl. No. 12/167,032, Non Final Office Action mailed Sep. 9, 2011", 14 pgs.
"U.S. Appl. No. 12/167,032, Non Final Office Action mailed Oct. 21, 2010", 16 pgs.
"U.S. Appl. No. 12/167,032, Response filed Feb. 17, 2011 to Non Final Office Action mailed Oct. 21, 2010", 10 pgs.
"U.S. Appl. No. 12/167,032, Response filed Aug. 29, 2011 to Final Office Action mailed Apr. 27, 2011", 9 pgs.
"U.S. Appl. No. 12/167,032, Response filed Sep. 30, 2010 to Restriction Requirement mailed Sep. 1, 2010", 6 pgs.
"U.S. Appl. No. 12/167,032, Response filed Nov. 22, 2011 to Non Final Office Action mailed Sep. 9, 2011", 8 pgs.
"U.S. Appl. No. 12/167,032, Restriction Requirement mailed Sep. 1, 2010", 6 pgs.
"U.S. Appl. No. 12/167,049, Applicant's Summary of Examiner Interview filed Feb. 9, 2012", 2 pgs.
"U.S. Appl. No. 12/167,049, Examiner Interview Summary mailed Jan. 26, 2011", 3 pgs.
"U.S. Appl. No. 12/167,049, Examiner Interview Summary mailed Jun. 29, 2012", 3 pgs.
"U.S. Appl. No. 12/167,049, Final Office Action mailed Aug. 31, 2010", 12 pgs.
"U.S. Appl. No. 12/167,049, Non Final Office Action mailed Mar. 28, 2012", 12 pgs.
"U.S. Appl. No. 12/167,049, Non Final Office Action mailed Dec. 18, 2009", 8 pgs.
"U.S. Appl. No. 12/167,049, Preliminary Amendment filed Jul. 3, 2008", 3 pgs.
"U.S. Appl. No. 12/167,049, Response filed Feb. 8, 2011 to Final Office Action mailed Aug. 31, 2010", 19 pgs.
"U.S. Appl. No. 12/167,049, Response filed Jun. 15, 2010 to Non Final Office Action mailed Dec. 18, 2009", 8 pgs.
"Canadian Application Serial No. 2,653,274, Office Action mailed Jan. 23, 2012", 3 pgs.
"European Application Serial No. 06784466.2, International Preliminary Report on Patentability mailed Nov. 30, 2007", 9 pgs.
"European Application Serial No. 06784466.2, International Search Report mailed Feb. 6, 2007", 7 pgs.
"European Application Serial No. 06813974.0, European Search Report mailed Jan. 12, 2010", 5 pgs.
"European Application Serial No. 06813974.0, Office Action mailed Apr. 8, 2008", 2 pgs.
"European Application Serial No. 06813974.0, Office Action mailed Apr. 14, 2010", 1 pg.
"European Application Serial No. 06813974.0, Response filed Oct. 21, 2010 to Office Action mailed Apr. 14, 2010", 17 pgs.
"European Application Serial No. 07762308.0, Office Action mailed Jan. 14, 2009", 2 pgs.
"European Application Serial No. 08828199.3, Office Action mailed May 11, 2010", 2 pgs.

(56) References Cited

OTHER PUBLICATIONS

"European Application Serial No. 08828199.3, Response filed Jun. 18, 2010 to Office Action mailed May 11, 2010", 9 pgs.
"European Application Serial No. 08828675.2, Office Action mailed May 11, 2010", 2 pgs.
"European Application Serial No. 08828675.2, Response filed Jun. 17, 2010 to Office Action mailed May 11, 2010", 2 pgs.
"European Application Serial No. 09774112.8, Office Action mailed Feb. 17, 2011", 2 pgs.
"European Application Serial No. 09774112.8, Office Action mailed Mar. 16, 2011", 1 pg.
"European Application Serial No. 09774112.8, Response filed Mar. 28, 2011 to Office Action mailed Feb. 17, 2011", 6 pgs.
"International Application Serial No. PCT/US2006/033893, International Preliminary Report on Patentability mailed Mar. 4, 2008", 4 pgs.
"International Application Serial No. PCT/US2006/033893, International Search Report mailed Jan. 29, 2007", (Jan. 29, 2007), 1 pg.
"International Application Serial No. PCT/US2006/033893, Written Opinion mailed Jan. 29, 2007", 3 pgs.
"International Application Serial No. PCT/US2007/069562, International Preliminary Report on Patentability mailed Nov. 28, 2008", 11 pgs.
"International Application Serial No. PCT/US2007/069562, International Search Report mailed Jul. 7, 2008", 1 pgs.
"International Application Serial No. PCT/US2007/069562, International Search Report mailed Jul. 7, 2008", 4 pgs.
"International Application Serial No. PCT/US2008/074616, International Preliminary Report on Patentability mailed Mar. 2, 2010", 6 pgs.
"International Application Serial No. PCT/US2008/074616, International Search Report mailed Dec. 16, 2008", 4 pgs.
"International Application Serial No. PCT/US2008/074616, Written Opinion mailed Dec. 16, 2008", 5 pgs.
"International Application Serial No. PCT/US2008/074642, International Preliminary Report on Patentability mailed Mar. 2, 2010", 5 pgs.
"International Application Serial No. PCT/US2008/074642, International Search Report mailed Feb. 12, 2009", 4 pgs.
"International Application Serial No. PCT/US2008/074642, Written Opinion mailed Feb. 12, 2009", 4 pgs.
"International Application Serial No. PCT/US2008/074645, International Preliminary Report on Patentability mailed Mar. 2, 2010", 6 pgs.
"International Application Serial No. PCT/US2008/074645, International Search Report mailed Dec. 29, 2008", (Dec. 29, 2008), 9 pgs.
"International Application Serial No. PCT/US2008/074645, Written Opinion mailed Dec. 29, 2008", 5 pgs.
"International Application Serial No. PCT/US2008/074655, International Preliminary Report on Patentability mailed Mar. 2, 2010", 6 pgs.
"International Application Serial No. PCT/US2008/074655, International Search Report mailed Feb. 18, 2009", 9 pgs.
"International Application Serial No. PCT/US2008/074655, Written Opinion mailed Feb. 18, 2009", 5 pgs.
"International Application Serial No. PCT/US2009/048456, International Preliminary Report on Patentability mailed Jan. 5, 2011", 7 pgs.
"International Application Serial No. PCT/US2009/048456, International Search Report mailed Apr. 27, 2010", (Apr. 27, 2010), 5 pgs.
"International Application Serial No. PCT/US2009/048456, Written Opinion mailed Apr. 27, 2010", 6 pgs.
"International Application Serial No. PCT/US2009/048476, Written Opinion mailed Dec. 10, 2009", 6 pgs.
"International Application Serial No. PCT/US2009/048481, Written Opinion mailed Dec. 10, 2009", 7 pgs.
"Japanese Application Serial No. 2008-529238, Office Action mailed Jan. 10, 2012", (W/ English Translation), 4 pgs.
"Japanese Application Serial No. 2008-529238, Office Action mailed Oct. 23, 2012", (W/ English Translation), 11 pgs.
"Japanese Application Serial No. 2008-529238, Response filed Apr. 2012 to Office Action mailed Jan. 10, 2012", (W/ English Translation), 9 pgs.
Lin, Feng-Huei, et al., "A study on bioglass ceramics in the Na2O-CaO-SiO2-P2O5 system", Journal of Materials Science, 23(12), (Dec. 1988), 4295-4299.
"U.S. Appl. No. 12/167,018, Final Office Action mailed Feb. 20, 2014", 9 pgs.
"U.S. Appl. No. 12/167,018, Non Final Office Action mailed Nov. 6, 2013", 9 pgs.
"U.S. Appl. No. 12/167,018, Response filed Feb. 4, 2014 to Non-Final Office Action dated Nov. 6, 2013", 14 pgs.
"U.S. Appl. No. 12/167,032, Non Final Office Action mailed Dec. 2, 2013", 8 pgs.
"U.S. Appl. No. 12/167,032, Response filed Feb. 25, 2014 to Non-Final Office Action dated Dec. 2, 2013", 12 pgs.
"U.S. Appl. No. 14/010,634, Non Final Office Action mailed Dec. 19, 2013", 10 pgs.
"European Application Serial No. 06813974.0, Examination Notification Art. 94(3) mailed Sep. 19, 2013", 4 pgs.
"European Application Serial No. 08827534.2, Response filed Jan. 28, 2014 to Office Action mailed Sep. 19, 2013", 9 pgs.
"Japanese Application Serial No. 2008-529238, Response filed Nov. 18, 2013 to Office Action mailed Aug. 20, 2013", (W/ English Translation of Claims), 6 pgs.

* cited by examiner

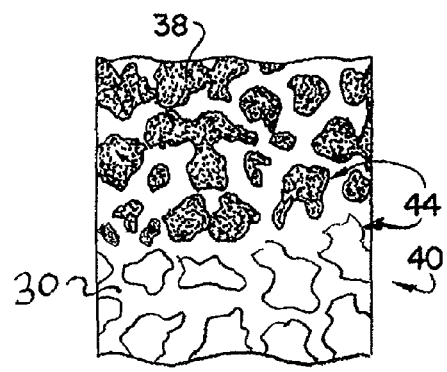
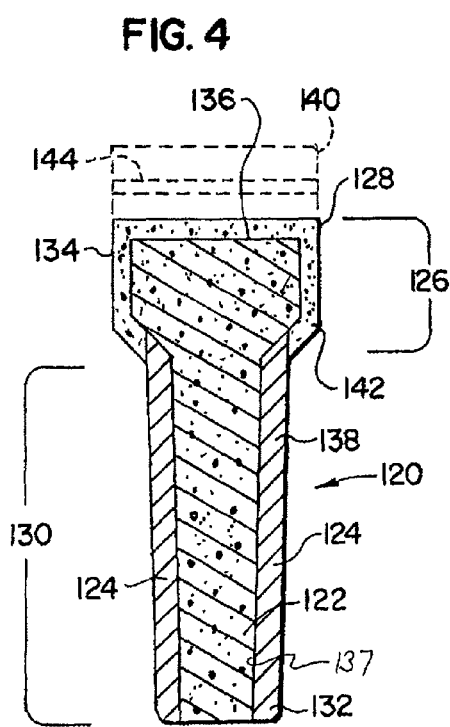
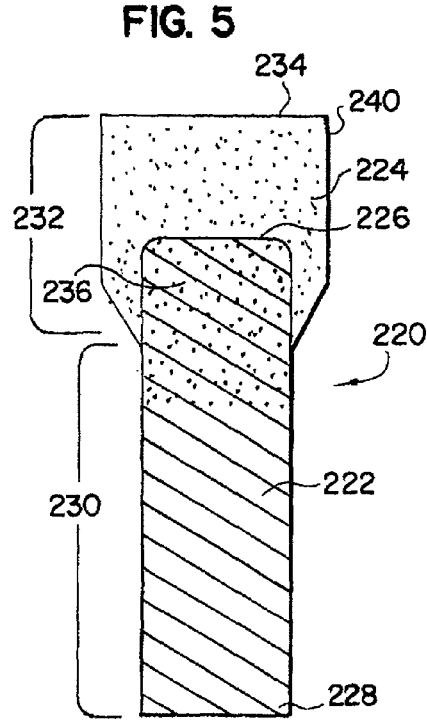

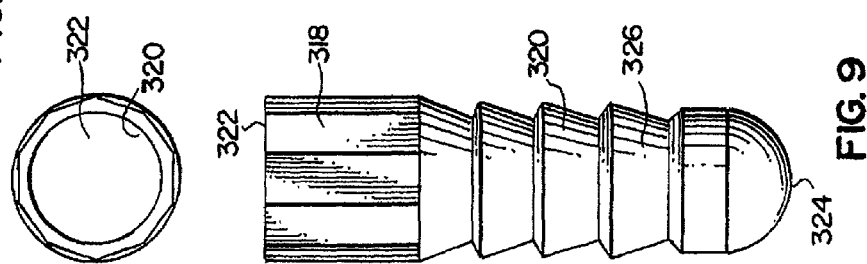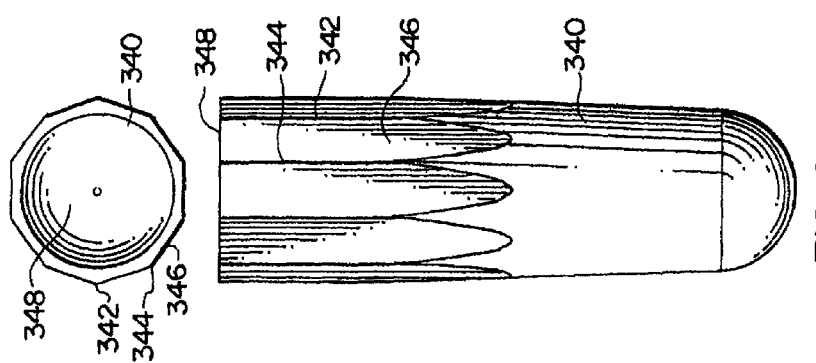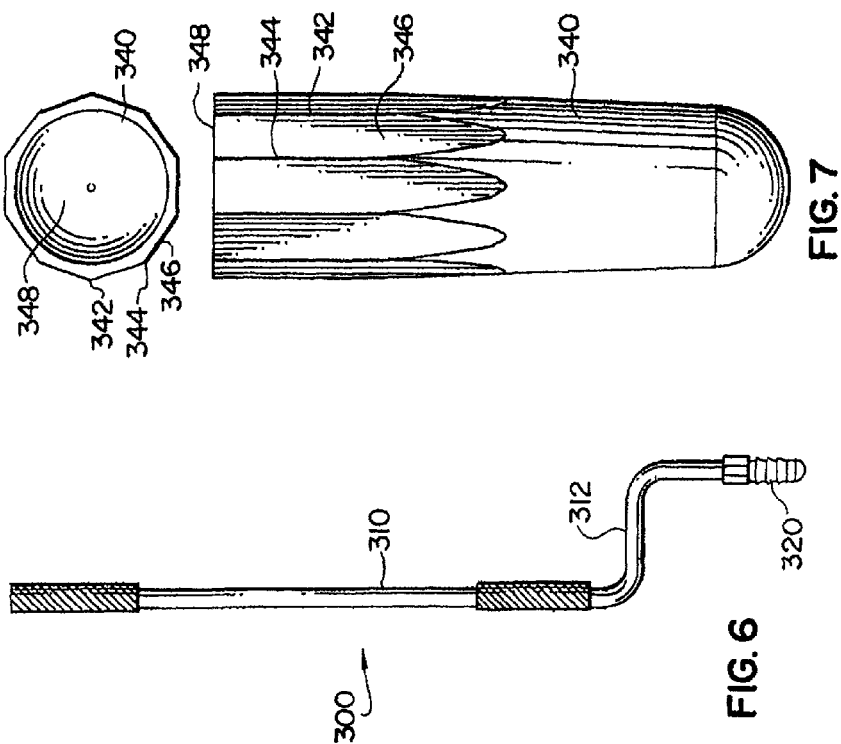

US 8,814,567 B2

DENTAL IMPLANT PROSTHETIC DEVICE WITH IMPROVED OSSEOINTEGRATION AND ESTHETIC FEATURES

CROSS-REFERENCE TO RELATED APPLICATIONS

This application is a continuation-in-part of International Application PCT/US2006/033893, with an international filing date of Aug. 30, 2006, which claims the benefit of U.S. Provisional Patent Application No. 60/712,577, filed Aug. 30, 2005, and this application is a continuation-in-part of pending U.S. patent application Ser. No. 11/622,171, filed Jan. 11, 2007, which is a continuation-in-part of pending U.S. patent application Ser. No. 11/420,024, filed May 24, 2006, which claims the benefit of U.S. Provisional Patent Application No. 60/684,743, filed May 26, 2005, all of which are incorporated herein by reference in their entirety for all purposes.

FIELD OF THE INVENTION

The present invention relates to dental implant prosthetic devices and, in particular, to a one-piece dental implant and prosthetic device with improved osseointegration and esthetic features, and a tool for insertion thereof into bone.

BACKGROUND OF THE INVENTION

A dental implant or fixture is surgically implanted into a patient's upper or lower jaw to directly or indirectly anchor and support prosthetic devices, such as an artificial tooth. The implants are usually placed at one or more edentulous sites in a patient's dentition at which the patient's original teeth have been lost or damaged in order to restore the patient's chewing function. In many cases, the implant anchors a dental abutment, which in turn provides an interface between the implant and a dental restoration. The restoration is typically a porcelain crown fashioned according to known methods.

One form of a prosthetic device is a unitary or one-piece implant device with a bone-engaging implant portion and an abutment portion integral with the implant portion. These devices are made of a suitable biocompatible material, such as titanium which is shown to provide adequate osseointegration characteristics. A desire still exists, however, to improve the osseointegration characteristics of such dental devices.

One problem with one-piece dental devices is that the titanium and other materials used for such devices often are an unattractive color. Thus, when the abutment portion of the device below a prosthetic tooth but above the gum or gingival tissue is visible and does not have the color of natural teeth, the dental device provides a non-esthetically pleasing appearance in a person's mouth. Other known dental devices that have the color of natural teeth typically provide inadequate strength resulting in relatively frequent replacement or repair of the device.

Whether or not the dental implant device is a one-piece implant or part of a multiple piece device where the abutment is assembled onto the implant, the implant is usually either threaded or press-fit into a bore which is drilled into the patient's mandible or maxilla at the edentulous site. The implant is inserted by applying a force to the coronal end of the implant in an insertion direction. For a threaded implant, self-tapping threads may be provided for initial stability of the implant immediately after surgery. Before biologic integration has time to take place, the threads resist tension, twisting, or bending loads applied to the implant. Additionally, patients prefer to leave the initial surgery with some type of restoration and it has further been shown that the healing of the soft and hard bone tissue is improved if the implant is loaded after surgery.

The surgical procedure for inserting the threaded implants, however, can be complicated and requires that the threaded implants be turned into place, which further requires the use of special tools and inserts. The torque needed to place the implant into the jaw can be high and may require tapping of the bore on the jaw, which adds yet another step to the surgical procedure where tapping typically is not desired. Also with threaded implants, it is often difficult to achieve optimal esthetics where, for example, a prosthetic is held at an ideal orientation by the implant because the geometry of the thread establishes a fixed relationship between the final vertical and rotational orientation of the implant such that a vertical adjustment requires a rotational adjustment and vice-versa.

Alternatively, a press fit implant has a much simpler surgical procedure. The current press fit designs, however, provide very little initial stability and are not well suited for early and immediate loading procedures that are currently used in dentistry.

BRIEF DESCRIPTION OF THE DRAWINGS

FIG. 3 is an enlarged sectional view of a porous tantalum portion and a filler material for a number of embodiments herein and in accordance with the present invention;

FIG. 4 is a cross-sectional view of a second embodiment of a one-piece dental implant prosthetic device in accordance with the present invention;

FIG. 5 is a cross-sectional view of a third embodiment of a one-piece dental implant prosthetic device in accordance with the present invention;

FIG. 6 is a side elevational view of an instrument used to aid in press-fitting an implant into a jaw bone in accordance with the present invention;

FIG. 7 is a side elevational view of an alternative implant configured for press-fitting in accordance with the present invention;

FIG. 8 is a top view of the alternative implant of FIG. 7;

FIG. 9 is a side elevational view of another implant configured for press-fitting in accordance with the present invention;

FIG. 10 is a top view of the implant of FIG. 9;

DETAILED DESCRIPTION

Figure 1:
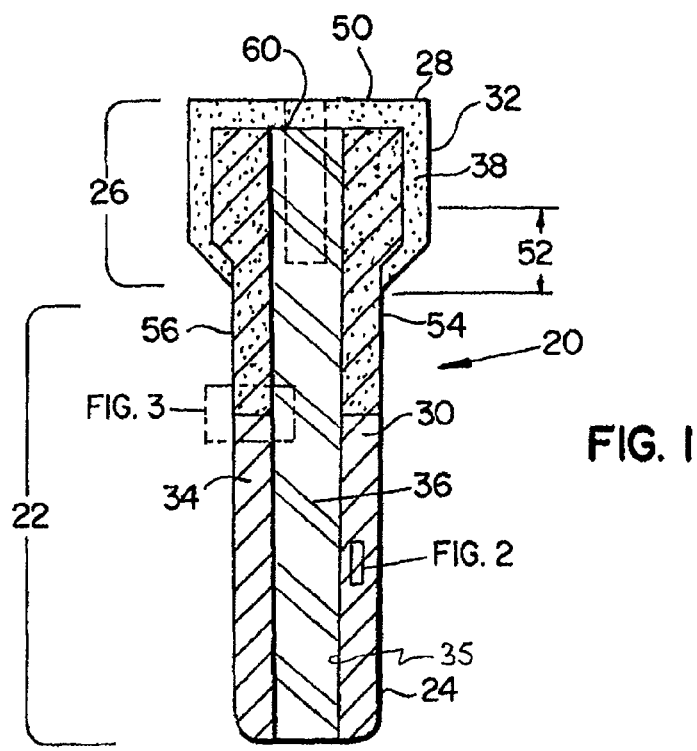
FIG. 1 is a cross-sectional view of a first embodiment of a one-piece dental implant prosthetic device in accordance with the present invention.

Referring to FIG. 1, there is illustrated a pre-fabricated one-piece dental prosthetic device 20. The one-piece dental device 20 has a bone engaging endosseous portion or implant portion 22 on a distal or apical end portion 24 of the device 20 to extend into the maxillae or mandible (either being otherwise generally referred to as the jaw bone). The implant portion 22 supports an abutment portion 26 integrally formed with the implant portion 22 and disposed at a proximal or coronal end portion 28 of the one-piece dental device 20. The abutment portion 26 may include an abutment, an integrally formed dental restoration (i.e., a (near) net-shape tooth or crown), and/or the transmucosal portion of a single stage dental implant. In the form shown in FIG. 1, the abutment portion 26 extends through and above the gingival tissue to support and receive a tooth shaped prosthetic or other types of prosthetic pieces or devices. The one piece dental device 20 also has a porous metal portion or matrix 30 to improve the osseointegration of the bone on at least the implant portion 22. Further, the one piece dental device 20 may have an outer portion 32 that has a color generally replicating the color of natural teeth so that if the abutment portion 26 is still exposed after a prosthetic is placed on the abutment portion, it will still have an aesthetic appearance in a person's mouth. The one-piece dental prosthetic device disclosed herein may also have other geometries, such as those found in U.S. patent application Ser. No. 11/380,569, which is incorporated herein by reference. These features are explained in detail below.

As mentioned, the porous metal portion 30 extends on the implant portion 22 where it can be placed in contact with the bone, and in one form, is a porous tantalum portion 40 which is a highly porous biomaterial useful as a bone substitute and/or cell and tissue receptive material. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is fully incorporated herein by reference. Other metals such as niobium, or alloys of tantalum and niobium with one another or with other metals may also be used.

Figure 2:
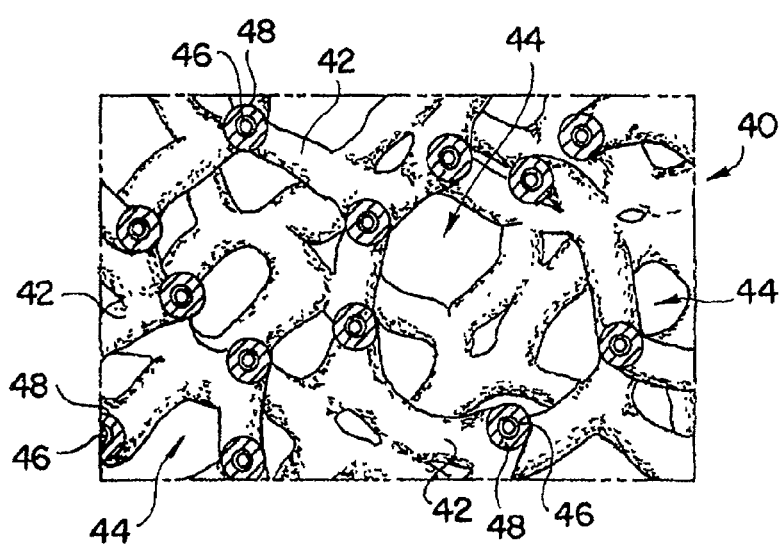
FIG. 2 is an enlarged fragmentary view of a porous tantalum portion for any of the embodiments herein and in accordance with the present invention.

Generally, as shown in FIG. 2, the porous tantalum structure 40 includes a large plurality of ligaments 42 defining open spaces 44 therebetween, with each ligament 42 generally including a carbon core 46 covered by a thin film of metal 48 such as tantalum, for example. The open spaces or pores 44 between ligaments 42 form a matrix of continuous channels having substantially no dead ends, such that growth of cancellous bone through porous tantalum structure 40 is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to anchor dental device 20 into the surrounding bone of a patient's jaw.

The porous tantalum structure 40 may be made in a variety of densities in order to selectively tailor the structure for particular applications. In particular, as discussed in the above-incorporated U.S. Pat. No. 5,282,861, the porous tantalum may be fabricated to many different desired porosity and pore sizes, and can thus be matched with the surrounding natural bone in order to provide an improved matrix for bone in-growth and mineralization. For example, the porous tantalum could be made denser with fewer pores in areas of high mechanical stress. This can be accomplished by filling all or some of the pores with a solid material which is described in further detail below.

Referring to FIG. 1, the porous metal portion 30 forms a sleeve 34 that at least partially surrounds a core 36. The sleeve 34, core 36, or both as shown may form a strong, reinforcing post that extends into the abutment portion 26 to reinforce the abutment. Here, the sleeve 34 substantially entirely encapsulates the core 36 although many other configurations are possible where the porous metal portion 30 covers only a part of the length or circumference of the core 36 whether continuously or spaced at intervals.

The core 36 is made of a suitable biocompatible material, such as titanium although the core 36 may also be made of other biocompatible materials such as at least one of the following: titanium alloy, stainless steel, zirconium, and cobalt-chromium-molybdenum alloy to name a few examples. The core 36 can be inserted into the sleeve 34 by various known methods such as press-fitting, diffusion bonding, or mechanical threading of the core 36 into the porous metal sleeve 34. Where the core 36 is press-fit into the sleeve 34, a fastening between the two parts is achieved by friction after the two parts are pushed together. The friction that holds the parts together is often greatly increased by compression of one part against the other, which relies on the tensile and compressive strengths of the materials of the engaged parts.

Diffusion-bonding of the core 36 and sleeve 34 is a solid-state joining process that involves holding components under load at an elevated temperature. The process is dependent upon a number of different parameters, such as time, applied pressure, bonding temperature and method of heat application. Alternatively, mechanically threading the core 36 into the sleeve 34 involves providing the sleeve with a threaded bore formed at its interior 35 which mates with a threaded male portion of the core 36.

The one-piece device 20 also may have an esthetic material (also referred to herein as an esthetic portion) 38 that has a color generally replicating the color of natural teeth. In this case, if the outer portion 32 has the esthetic portion 38 and is disposed on the abutment portion 26, for example, and the outer portion 32 is exposed even when a temporary or final prosthesis is placed on the abutment portion 26, the exposed outer portion 32 will still provide an esthetically pleasing appearance.

The esthetic portion 38 may comprise either a polymer, a composite material as disclosed in detail in commonly owned U.S. patent application Ser. Nos. 11/420,024 and 11/622,171, which are fully incorporated herein as mentioned above, or a ceramic material. When the esthetic portion 38 comprises composite materials it may include the combination of a matrix material, a reinforcing material and a colorant. The matrix material may be a polyaryl ether ketone (PAEK) such as polyether Ketone Ketone (PEKK), polyether ether ketone (PEEK), polyether ketone ether ketone ketone (PEKEKK), polymethylmethacrylate (PMMA), polyetherimide, polysulfone, and polyphenylsulfone. The polymers can also be a thermoset material including, without limitation, bisphanol glycidyl methacrylate (Bis-GMA), urethane dimethacrylate (UDMA), methylmethacrylate (MMA), triethylene glycol dimethacrylate (TEGDMA), a combination of thermoset plastics, or a combination of thermoset and thermoplastics. Additionally, they can be comprised of, without limitation, a large class of monomers, oligomers and polymers, such as acrylics, styrenics and other vinyls, epoxies, urethanes, polyesters, polycarbonates, polyamides, radiopaque polymers and biomaterials.

The reinforcing material may comprise, to name a few possible examples, at least one selected from the group comprising carbon, $Al_2O_3$, $ZrO_2$, $Y_2O_3$, $Y_2O_3$-stabilized $ZrO_2$, MgO-stabilized $ZrO_2$, E-glass, S-glass, bioactive glasses, bioactive glass ceramics, calcium phosphate, hydroxyapatite, $TiO_2$, Ti, $Ti_6Al_4V$, stainless steel, polyaryl ether ketones (PAEK) such as polyethyl ethyl ketone (PEEK), polyethyl ketone ketone (PEKK), and an aramid. The geometry of the reinforcing material may include fibers, particulates, variable diameter fibers and fibers fused with particulates on the fiber surfaces. The colorant may be titanium dioxide as one example.

In one example, the esthetic portion 38 may comprise about 55% by weight of the composite material PEKK as the matrix material, about 35% by weight of the composite material of E-glass fibers as the reinforcing material, and about 10% by weight of the composite material of titanium dioxide particles as the colorant. In another example, the esthetic portion 38 may comprise about 53% by weight of the composite material PEKK as the matrix material, about 35% by weight of the composite material of E-glass fibers as the reinforcing material, and about 12% by weight of the composite material of titanium dioxide particles as the colorant.

In one form, the outer portion 32 has an exterior separate from the porous tantalum portion so that the outer portion is substantially free of the porous tantalum portion. This results in the exterior of the outer portion 32 forming a smooth skin layer comprised substantially of the esthetic material, where the skin layer of esthetic material may have a thickness of approximately 0.05 to about 3.0 mm. Furthermore, the smooth skin layer of the outer portion 32, when placed along the implant portion 22 or within the transmucosal layer 52 (i.e., gingival region of the prosthetic) on the abutment portion 26, forms a relatively solid, pore-free outer layer. This limits attachment of soft tissue and bacteria onto the outer portion 32 and limits the in-growth of the epithelium so that it does not interfere with bone growth against the implant portion 22. The outer portion 32 may be disposed on at least one of a coronal end of the coronal end portion 28, a side of the coronal end portion 28, and the transmucosal layer 52 on the abutment portion 26, but preferably on substantially all three areas. Thus, a smooth, non-porous outer portion 32 may be provided from the upper end 50 on the abutment portion 26, along the transmucosal region 52 of the abutment portion, and in one case, down to the point where the abutment portion 26 narrows and ends and the implant portion 22 begins. In another form, as shown, a smooth surface 54 may also be provided on the coronal end 56 of the implant portion 22 if desired.

Referring to FIGS. 1 and 3, in another form, the esthetic portion 38 may at least partially impregnate the porous metal portion 30 so that the esthetic portion acts as a filler material and/or the porous metal portion 30 reinforces the esthetic portion 38. In such cases, the esthetic portion 38 fills at least a portion of the pores 44 of the porous metal portion 30. In one form, the esthetic portion 38 substantially completely fills the pores 44 near the coronal end 56 of the implant portion 22 and forms the smooth exterior skin layer 54 mentioned above. The pores 44 of the porous metal portion 30 near the distal end or apical end 24 of the implant portion 22 are substantially free of the esthetic material 38, which allows in-growth of bone to anchor the one-piece dental device 20 to the jaw. Accordingly, there can be a general, internal dividing line above which the porous tantalum is substantially impregnated with esthetic material and below which it is not, similar to the diagram in FIG. 3, and applicable to any of the dental implant devices described herein.

To impregnate the porous metal portion 30 with the esthetic portion 38, the polymers or composites that make up the esthetic material can be injection-molded into the porous metal portion 30 such as on the sleeve 34, so that the polymer or composite material infiltrates the vacant open spaces 44 forming a solid mass of the polymer or composite material with metal reinforcement. Furthermore, injection-molding of the polymer or composite material may also be used to form the non-porous skin layer with the outer portion 32 as described above.

The esthetic portion 38 can also be reinforced by the porous metal portion 30 by an insert-molding process. Insert molding is an injection molding process whereby the esthetic portion 38 is injected into a cavity and around an insert piece, such as the sleeve 34 of porous tantalum, placed into the same cavity just prior to molding, resulting in a single piece with the insert encapsulated by the esthetic portion 38. The impregnation of the porous tantalum portion 30 as shown in FIG. 3 was performed by insert-molding.

Mechanical bonding also takes place during the insert molding process. Mechanical bonding can occur by shrinking of the esthetic portion 38 around the sleeve 34 as the esthetic portion cools or by filling in irregularities in the surface of the sleeve 34. Mechanical bonding further can occur when the esthetic material 38 infiltrates the open spaces within the pores 44 of the porous sleeve 34.

When the esthetic portion 38 is composed of a ceramic material, such as dental porcelain, the ceramic material can be placed in the porous metal portion 30 via sintering and an enameling process. The enameling process includes fusing powdered glass to the porous metal portion 30 by firing at extremely high temperatures. The ceramic powder can melt and flow, and hardens into a smooth, durable ceramic coating that can be placed on the porous tantalum portion and can be inlaid within the pores 44 of the porous tantalum portion. The ceramic material, after firing and cooling, becomes a smooth, hard and very durable material.

A microscopic model can be obtained to predict the overall mechanical properties of the porous metal/composite material-filled structure. For instance, a relationship between the strength of the porous metal/composite material and the strength of a particular filler material (shown in FIG. 11) can be obtained by using a finite element model (as shown in FIG. 12). More specifically, the prediction of the porous metal/composite material structure's overall mechanical behavior can be based on Representative Volume Element (RVE) theory. The RVE theory comprises constructing a representative portion of the material's microstructure (an "RVE") and subjecting it to virtual testing. The overall mechanical behavior of the RVE is found to be equivalent to the composite material it represents.

As an example, an RVE program such as commercially available FE software, ANSYS version 10 (available from ANSYS, Inc., Canonsburg, Pa., USA) is used to generate a two-dimensional stochastic Voronoi cell structure based on RVE theory to simulate random microscopic struts of the porous metal at the microscopic level. Specifically, the porous metal/composite material structure was meshed using 8-node hexagon mesh. The porous metal structure was simulated using tantalum metal material properties as a bi-linear, elasto-plastic material (i.e., having Young's Modulus E=179 GPa, Poisson's ratio $\mu$=0.34, Yield stress $\sigma y$=190 MPa and Tangent Modulus Et=17 GPa). The pores between the struts were modeled to be impregnated with a composite material as a filler material similar to that shown in FIG. 3 except all pores were filled for the test. The filler composite material was modeled as a linear elastic material having a varied elastic modulus and Poisson's ratio equal to 0.4.

To compute the overall Young's modulus (E) of the structure, a boundary condition was applied to the finite element model as shown in FIG. 12 to simulate compression testing. The finite element model has a fixed, constrained face with an area ($A_{xx}$) formed by a length in the x direction ($D_x$) and a length in the y direction ($D_y$). All other faces are unconstrained along the x-direction. The boundary or test condition used was to apply a uniform strain field with 0.1% strain along the x-direction to the RVE and the finite element model. For instance, in order to compute $E_{xx}$ (Young's modulus along the x-direction), a displacement $U_x$ represents an applied strain where $U_x=0.001D_x$. Therefore, $E_{xx}$ can be computed as follows:

$$E_{xx} = 1000 \times \frac{\sum R_x}{A_{xx}}$$

where $\Sigma R_x$ represents the summation of reaction forces at the constrained faces. Due to its structural symmetry, the Young's modulus along the x, y and z directions is the same. Therefore, $E=E_{xx}=E_{yy}=E_{zz}$.

Figure 11:
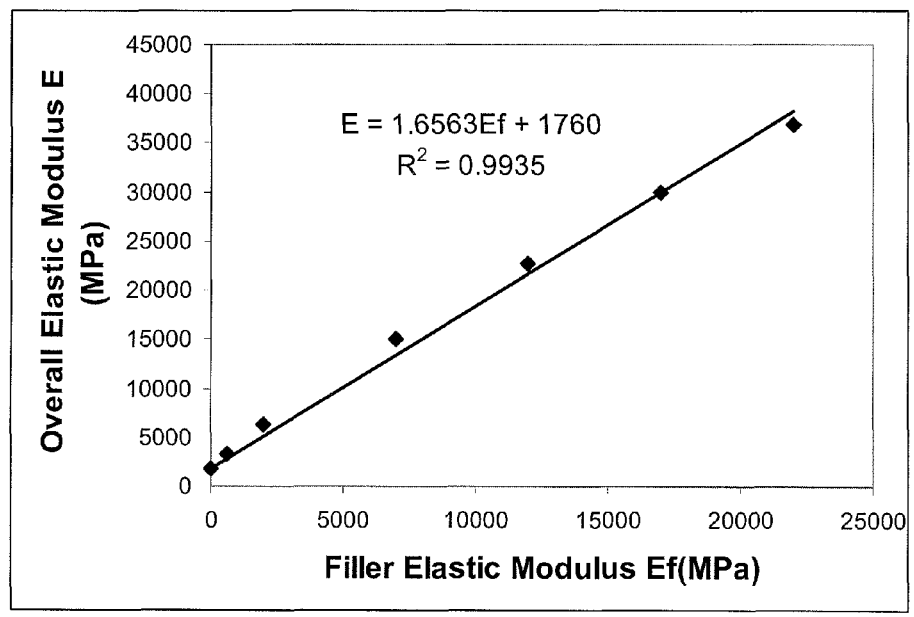
FIG. 11 is a graphical representation of the overall elastic modulus for a porous metal/composite material structure as a function of an elastic modulus of a filler material for the structure.
Figure 12:
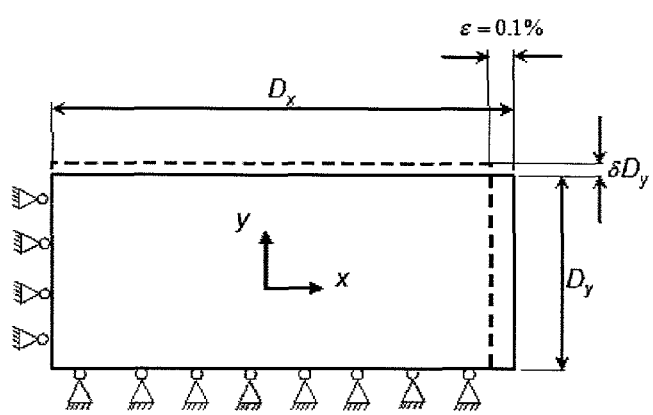
FIG. 12 is a schematic diagram showing the boundary conditions used for computing Young's modulus for the porous metal/composite material structure shown graphically in FIG. 11.

As a result, the overall elastic modulus, E, of the porous metal impregnated with the composite material was plotted versus the filler (i.e., composite material) elastic modulus, $E_f$, and is shown in FIG. 11. A linear regression was used to fit the data points and an equation was obtained expressing the overall elastic modulus, E, for the porous metal/composite material structure as a function of the filler elastic modulus, $E_f$, or $E=1760+1.6563\ E_f$, and further having an R-squared value of 0.9935, where R-squared is a statistical measure of the fraction of variance expressed by the model.

In another form, the one-piece dental device 20, as well as the other implants described below, may have multiple textured surfaces as described in detail in U.S. Pat. No. 5,989,027, assigned to the assignee of the present invention, the disclosure of which is expressly incorporated herein by reference. For example, the sleeve 34 of porous tantalum may have an increasing porosity from the proximal end 28 toward the distal end 24 of the one-piece dental device 20. Thus, the sleeve 34 may be formed of substantially solid, non-porous tantalum near the proximal end 28, within the transmucosal region 52 on the abutment portion 26, and/or slightly distally of the abutment portion 26 to provide a seal with the surrounding gingiva such that plaque or bacteria cannot lodge on or deposit within the sleeve 34 near the gumline of the patient should the upper portion of the sleeve 34 be exposed to the oral cavity. Alternatively, the surface of the abutment portion 26 of the core 36 could be formed of smooth, polished titanium or other materials providing such a smooth, solid finish to allow ready removal of bacterial plaque deposits by conventional oral hygiene techniques. As another option, bands of titanium or other materials may be provided with a solid yet roughened surface, such as at the coronal end 56 of the implant portion 22 to promote some bone growth while still limiting at least some soft-tissue and bacterial growth.

In addition to these approaches, the porosity of the porous metal portion 30 of the sleeve 34 can increase gradually or at intervals as desired and as the sleeve 34 extends distally to promote maximum bone in-growth and osseointegration at the distal end portion 24 of the one-piece dental device 20. For this purpose, the pores 44 of the porous metal structure 30 may be formed with increasingly larger sizes from the proximal end portion 28 to the distal end portion 24 of the one-piece dental device 20.

Also, the sleeve 34 may be attached to the core 36 of the one-piece dental device 20 in a manner wherein, after osseointegration of the sleeve 34 into the surrounding bone, the core 36 is slightly movable relative to the sleeve 34 in order to dissipate forces which are imposed upon the one-piece dental device 20, such as mastication forces, for example. In one embodiment, the sleeve 34 may be secured to the core 36 via an adhesive or cement material which is slightly compressible, such that when mastication or other forces are imposed upon the abutment portion 26, the core 36 may move slightly relative to the sleeve 34 whether within the abutment portion 26 or within the implant portion 22. Such adhesive or cement materials include acid-base reaction formulations such as zinc phosphate, zinc oxide/eugenol, zinc polycarboxylate, glass ionomer, or resin based formulations similar to that of resin-based dental restorative filling materials. One specific example is a dental adhesive/bonding agent that is composed of monomers of hydroxyethyl methacrylate (HEMA), 4-methacryloxyethyl trimellitate anhydride (4-META) and an organophosphate (e.g., 10-methacryloyoxydecamethylene phosphoric acid, MDP). In other embodiments, a compression ring, a spring, or another type of "shock absorbing" structure may be fitted between the core 36 and the sleeve 34 to allow for relative movement therebetween.

Referring to FIG. 4, there is illustrated a one-piece dental device 120 that similarly includes a core 122 and a porous metal portion 124 in the form of a sleeve 138 that at least partially surrounds the core 122 and may be made of a porous tantalum such as Trabecular Metal™. The dental device 120 also has an abutment portion 126 at a proximal end portion 128 of the one-piece dental device 120 and an implant portion 130 at a distal end portion 132 of the one-piece dental device 120. An outer portion 134 having an esthetic material 142, similar to esthetic material 38, has a color generally replicating the color of natural teeth and is disposed at least at the abutment portion 126 of the device 120 as described further below.

For the one-piece dental device 120, the core 122 also is made of a porous metal such as tantalum and may be received by an interior or bore 137 of the sleeve 138. The core 122 can be inserted into the sleeve 138 by various methods such as press-fit or mechanical threading as described above. Alternatively, the sleeve 138 may be integrally formed with the core 122. While the porous metal portion 124 generally remains on the implant portion 130 (i.e. it does not extend substantially onto the abutment portion 126 in this example), the porous metal core 122, in one form, widens and forms the bulk of the abutment portion 126 and forms a strong, reinforcing post that extends from within the implant portion 130 to within the abutment portion 126. Thus, in this case, the porous metal, and therefore, the porous metal portion 134, may be described as generally extending throughout the prosthetic device 120.

For the dental device 120, the core 122 is impregnated with a filler while the porous metal portion 124 forming the sleeve 138 and that forms the exterior of the implant portion 130 for engaging bone is substantially free of the esthetic material. The filler may be a composite or polymer material, which may be the same as the esthetic material 142, and may fill in the vacant open spaces in the porous tantalum as previously discussed above with the embodiment of FIG. 1 and as shown in FIG. 3, except that here, the composite or polymer material fills the pores of the entire length of the core 122 from the proximal end portion 128 to the distal end portion 132. The core 122 may be impregnated by any of the previously discussed methods, such as by injection-molding.

The esthetic material or esthetic portion 142 of the one-piece dental device 120, as mentioned above for the dental device 20, may be disposed at least the outer portion 134 at the abutment portion 126 for esthetics and to at least partially cover the porous tantalum portion of the core 122 at the proximal portion 128 to limit gingival tissue growth there. Thus, at the proximal end portion 128 of the core 122, the outer portion 134 forms a smooth esthetic skin layer that is substantially free of porous tantalum, and is located around substantially the entire abutment portion 126. The outer portion 134 may have a skin layer that is approximately 0.05 to about 3.0 mm thick. With this configuration, the porous sleeve 138 substantially covers the implant portion 130 of the outer layer of the implant 120 to promote bone growth while the exposed abutment portion 126 with a solid, smooth esthetic outer surface limits the in-growth of soft tissue and bacterial growth against the abutment portion 126.

In one variation of the one-piece dental device 120, a thickened, outer and upper portion or layer 140 is formed coronally of the core 122 at the coronal end portion 128 and is made of the esthetic material. The upper layer 140 can be formed by injecting the esthetic material onto the porous structure of the tantalum core 122 until a coronal or terminal end 136 of the core 122 is coated with several millimeters of esthetic material. The layer 140 is substantially free of porous metal so that it can be easily shaped by a practitioner for receiving another dental device or restoration such as a dental prosthesis or final crown, for example.

In another alternative, one or more gaps 144 within the upper layer 140 encourages soft tissue in-growth to form a seal around the perimeter of the implant 120 at the location of the gap 144. This seal coupled with the non-porous outer surface formed by the esthetic portion 142 on the abutment portion 126 forms a barrier that limits bacteria, epithelium or other contaminants from passing through the porous metal and into a bone integration area along the implant portion 130. While the gap 144 is shown as a continuous gap around the upper layer 140 it will be appreciated that many other forms are possible, such as non-continuous gaps, spaced holes, or other uniform or more randomly placed openings, to name a few examples.

Referring to FIG. 5, there is illustrated a third embodiment of a one-piece dental device 220 including a porous metal portion 222 of tantalum or other materials as described above, and an outer portion 240 having a color generally replicating the color of natural teeth and formed by an esthetic portion or material 224 on an abutment portion 232. The porous tantalum portion 222 forms an implant portion 230 at a distal or apical end portion 228 of the dental device 220. The porous metal portion 222 also forms a reinforcing core 236 of the abutment portion 232 at the coronal end portion 234 of the dental device 220. While the core 236 is shown to extend approximately half the height of the abutment portion 232, it will be understood that other variations are possible including the core 236 extending at or near the terminal coronal end 234 of the abutment portion 232 or being much shorter such that the core 236 extends a relatively small distance into the abutment portion 232. In the form illustrated, the core 236 does not extend near the terminal coronal end 234 so that the esthetic portion 224 disposed coronally of the core 236 is separate from the porous metal portion 222 and is substantially free of porous metal so that the end 234 is easily shaped similar to coronal upper layer 140 of dental device 120 (FIG. 4).

In one form, pores are provided generally throughout the porous tantalum portion 222 from a coronal or proximal end 226 of the porous metal portion 222 to the apical end portion 228, and through the implant portion 230. The porous metal portion 222 has pores at least partially impregnated with the esthetic portion 224. The pores at the apical end portion 228 are substantially free of esthetic material while the pores at the coronal end portion 226 are at least partially impregnated with the esthetic material. In one form of device 220, the pores that are substantially free of esthetic material form the majority of the implant portion 230 although other variations are contemplated.

It will also be appreciated that while the porous metal portion 222 is shown to form substantially the entire implant portion 230, other outer sleeves or layers on the porous metal portion 222, whether presenting a solid and/or porous outer surface, may be provided as with the other alternative embodiments described.

It will further be appreciated that the outer portion 240 may be located on any outer part of the abutment portion 232 and may be substantially free of the porous tantalum portion as with the other embodiments herein. The outer portion 240 may contain a smooth exterior layer that has a minimal width of about 1 mm on the sides of the core 236 and/or may have a substantial thickness of about 1 to about 5 mm above the coronal end 226 of the core 236.

Referring again to FIG. 1, to surgically implant the one-piece dental device 20, or any of the implant devices herein, the one-piece dental device 20 may be fitted into a bore drilled into a patient's jaw bone at an edentulous site. In particular, the one-piece dental device 20 may be impacted or press-fitted into the bore to provide a firm initial seating of the one-piece dental device 20 into the bore. For this purpose, the dental device 20 may have a tool or driver-engaging structure 60 such as a bore (shown in dashed line) for receiving a driver to insert the dental device 20 into the bone tissue. The bore 60 may use structures, such as an interference fit, for releasably engaging the driver. Thereafter, the bone tissue surrounding the one-piece dental device 20 may osseointegrate into the open spaces 44 of the porous sleeve 34, thereby firmly anchoring the sleeve 34 and the one-piece dental device 20 into the surrounding bone structure. Thereafter, a temporary or permanent prosthesis may be secured to the esthetic portion 38 in a known manner when the esthetic portion 38 includes an abutment.

Referring to FIGS. 6-10, a press-fitting driver 300 may be used to press fit one-piece dental devices such as those described above or other implants such as implants 320 and 340. Thus, while driver 300 is described with the use of implant 320, any of the implant-devices described herein may be used similarly with the driver 300.

When press-fitting a dental device 320, for example, into a bore on the jaw, it may be desirable to make the fit between the surgical site and the press-fit implant very tight so that the dental device 320 can achieve the required degree of stability for immediate or early loading. To achieve the desired tight fit, it may be difficult to press-fit the dental device 320 into the bore by hand pressure alone. Therefore, a driver 300 may be used to apply pressure to properly press-fit the implant into the bore to achieve a tight fit. In contrast to osteotomes, the driver 300 is fastened directly to the dental device 320 or to an implant carrier, rather than to the jaw site. A single drill can be used to create a pilot hole, or bore, in the jaw and the tip 324 of an implant 320 can be placed into the hole. The driver 300 can be attached to the implant 320 on the end 322 that is opposite the apical tip 324 and a proximal portion or handle 310 of the driver 300 can then be struck with a mallet or other driving tool to deliver a greater force to the implant 320 than could be done by hand in order to achieve the tight fit with the hole. The driver 300 may have a bent portion 312 that extends to, and orients, the proximal portion 310. So configured, the proximal portion 310 is oriented in a certain position and direction (i.e., facially of the jaw) so that an object, such as the mallet, other tool, or even a person's hand has convenient access to the proximal portion 310 away from the area directly between the teeth and outside of the mouth where there is more space to maneuver. The coronal end 322 of the implant 320 may be flat to engage the driver 300 or may have a bore similar to bore 60 on the one-piece dental device 20 (FIG. 1) for receiving the driver 300.

Referring to FIGS. 7-10, in order to facilitate the early loading of the implant devices, the implant devices 320 and 340 may be generally or substantially cylindrical and may have a taper so that the coronal end has a larger diameter than the apical end of the implant device to expand the bone as the implant device is inserted to create a relatively strong interference fit. Alternatively, or additionally, implant device 340 is provided with a polygonal portion 342 so that vertices 344 at the edges of sidewalls 346 of the polygonal portion 342 penetrate the usually cylindrical sides of a bore formed by a dental drill. So configured, twisting or rotation of the implant device 340 is resisted. Forming the polygonal portion 342 of the porous metal as described above adds further frictional resistance against the walls of a bore in the jaw. While the polygonal portion 342 may be sized and shaped to resist rotation, it should also be shaped with a width (and number of vertices) that does not create an unmanageable resistance to translating the implant device 340 for vertically inserting the implant 340 into the bore of the jaw. Thus, it will also be understood that the polygonal portion 346 may extend the entire length of the implant 340 or any other length that is advantageous for resisting rotation but that the longer the polygonal shape along the implant 340, the more difficult it may be to insert the implant 340 into a circular bore.

Referring again to FIGS. 9 and 10, in addition to a polygonal portion 328, the implant 320 also has a plurality (but at least one) of annular teeth 326 that taper outward as the teeth extend coronally. This is provided in order to increase resistance to pull-out, which is strengthened further when the teeth are formed of friction-increasing porous metal as described herein. It will be understood that the features shown on implants 320 and 340 may be provided for any of the one-piece dental devices described herein.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A pre-fabricated one-piece dental prosthetic device, comprising:
    a porous portion defining a longitudinal axis and having a first side substantially parallel to the longitudinal axis, the porous portion defining an abutment portion and an implant portion, wherein the implant portion is inserted into and engaging bone when the dental prosthetic device is implanted, and wherein the abutment portion is configured to extend above a transmucosal region of the prosthetic device and receive a prosthesis; and
    an outer portion having a color generally replicating the color of natural teeth, the outer portion disposed on at least a portion of the abutment portion, along a portion of the transmucosal region, and to a point along the implant portion at the first side, the outer portion oriented to taper toward the porous portion until an exterior surface of the outer portion intersects the first side of the porous portion, the abutment portion extending above where the exterior surface of the outer portion intersects the first side of the porous portion.

2. The pre-fabricated one-piece dental prosthetic device of claim 1, further comprising an esthetic portion disposed proximal to at least the outer portion, and wherein the porous portion is disposed and arranged for reinforcing the esthetic portion.

3. The pre-fabricated one-piece dental prosthetic device of claim 1, wherein the porous portion being at least in part impregnated with esthetic material having a color generally replicating the color of natural teeth.

4. The pre-fabricated one-piece dental prosthetic device of claim 1, wherein the implant portion includes a bone engaging portion.

5. The pre-fabricated one-piece dental prosthetic device of claim 1, further comprising a core portion, and wherein the porous portion at least partially surrounds the core portion.

6. The pre-fabricated one-piece dental prosthetic device of claim 5, wherein the core portion comprises at least one metal selected from the group consisting of titanium, titanium alloy, stainless steel, zirconium, and cobalt-chromium-molybdenum alloy.

7. The pre-fabricated one-piece dental prosthetic device of claim 5, wherein the core portion comprises porous tantalum having pores at least partially impregnated with esthetic material.

8. The pre-fabricated one-piece dental prosthetic device of claim 1, further comprising an endosseous portion with a proximal portion, and wherein the outer portion at least partially covers the porous portion at the proximal portion to limit gingival tissue growth on the proximal portion.

9. The pre-fabricated one-piece dental prosthetic device of claim 1, wherein the porous portion defines a plurality of pores, and wherein esthetic material substantially fills the pores of the porous portion.

10. The pre-fabricated one-piece dental prosthetic device of claim 1, wherein the porous portion generally extends throughout the prosthetic device.

11. The pre-fabricated one-piece dental prosthetic device of claim 1, further comprising a coronal end portion integrally formed with a bone implant part, and wherein the porous portion is formed at the bone implant part, and wherein the coronal end portion includes the outer portion.

12. The one-piece dental prosthetic device of claim 1, wherein the outer portion has an exterior separate from the porous portion.

13. The pre-fabricated one-piece dental prosthetic device of claim 1, further comprising an esthetic portion disposed proximal to at least the outer portion, and wherein the esthetic portion comprises at least one of a polymer, a composite material, and a ceramic.

14. A pre-fabricated one-piece dental prosthetic device comprising:
    an abutment portion extending coronally with respect to a jaw bone and gingiva disposed on the jaw bone and configured to support a prosthetic tooth, the abutment portion having a transmucosal region, the abutment portion oriented to taper in the transmucosal region toward a porous metal matrix until an exterior surface of the abutment portion intersects the porous metal matrix;
    an implant portion integrally formed with the abutment portion and inserted into and engaging bone when the dental prosthetic device is implanted;
    a post; and
    the porous metal matrix disposed adjacent to the post, wherein the post and the porous metal matrix extend from an apical end of the implant portion to above where the exterior surface of the abutment portion intersects the porous metal matrix and above the transmucosal region, and wherein the porous metal matrix has a part extending within the abutment portion such that a portion of the porous metal matrix extends above the gingival tissue of the jaw bone.

15. The pre-fabricated one-piece dental prosthetic device of claim 14, wherein the abutment portion further comprises an esthetic portion having a color generally replicating the color of natural teeth.

16. The pre-fabricated one-piece dental prosthetic device of claim 15, wherein the porous metal matrix has pores at least partially impregnated with esthetic material.

17. The pre-fabricated one-piece dental prosthetic device of claim 15, wherein the esthetic material substantially fills the pores.

18. The pre-fabricated one-piece dental prosthetic device of claim 15, wherein the part is impregnated with the esthetic portion.

19. The pre-fabricated one-piece dental prosthetic device of claim 15, wherein the esthetic portion forms an outer surface on the implant portion to limit gingival tissue attachment to the implant portion.

20. The pre-fabricated one-piece dental prosthetic device of claim 14, wherein the post further comprises a core made of at least a metal selected from the group consisting of titanium, titanium alloy, stainless steel, zirconium, and cobalt-chromium-molybdenum alloy.

21. The pre-fabricated one-piece dental prosthetic device of claim 14, wherein the post has a greater width within the abutment portion than at the implant portion.

22. The pre-fabricated one-piece dental prosthetic device of claim 14, wherein the porous metal matrix comprises tantalum.

23. A pre-fabricated one-piece dental prosthetic device, comprising:
    an abutment portion configured to support a prosthesis, the abutment portion at least partially made of a filler material and porous metal having pores, wherein at least some of the pores of the porous metal are impregnated with the filler material, the abutment portion including a non-porous outer layer disposed on at least a portion of the abutment portion, the outer layer made at least partially of an esthetic material having a color generally replicating the color of natural teeth; and
    an apical portion integrally formed with the abutment portion, the apical portion configured to engage bone, wherein the porous metal is configured to extend from above a transmucosal region of the abutment portion down to an apical end of the apical portion.

24. The pre-fabricated one-piece dental prosthetic device of claim 23, wherein the filler material is the same material as the esthetic material.

25. The one-piece dental prosthetic device of claim 23, wherein the outer layer is disposed on at least one of:
    a coronal end of the abutment portion, a side of the abutment portion, and
    a gingival region of the prosthetic device.

26. A dental prosthetic device, comprising:
    a dental implant having a porous portion defining an abutment portion configured to receive a prosthesis and an implant portion configured to be inserted into and engage bone when the dental prosthetic device is implanted, the porous portion extending from an apical end of an implant portion to a coronal end of the abutment portion, and the porous portion configured to extend from within a jaw bone to above both the jaw bone and gingiva disposed on the jaw bone when the dental implant is fully assembled on the jaw bone; and
    a non-porous outer layer having a color generally replicating the color of natural teeth, the non-porous outer layer disposed on at least a portion of the abutment portion.

* * * * *